United States Patent [19]
Mead et al.

[11] Patent Number: 5,472,872
[45] Date of Patent: Dec. 5, 1995

[54] RECOMBINANT CVIJI RESTRICTION ENDONUCLEASE

[76] Inventors: David Mead, 2301 Waltham Rd.; Neela Swaminathan, 476 Presidential La., both of Madison, Wis. 53711; James Van Etten, 7409 Stevens Ridge Rd., Lincoln, Nebr. 68516; Piotr Skowron, 7400 W. Center St., Wauwatosa, Wis. 53210

[21] Appl. No.: 181,629

[22] Filed: Jan. 13, 1994

[51] Int. Cl.⁶ .................... C12N 15/70; C12N 15/54
[52] U.S. Cl. ............... 435/252.33; 435/193; 435/194; 435/320.1; 536/23.2
[58] Field of Search .................... 435/199, 193, 435/320.1, 252.33; 536/23.2

[56] References Cited

U.S. PATENT DOCUMENTS

| | | | |
|---|---|---|---|
| 5,137,823 | 8/1992 | Brooks | 435/199 |
| 5,196,331 | 3/1993 | Wilson et al. | 435/69.1 |
| 5,200,333 | 4/1993 | Wilson | 435/172.3 |

OTHER PUBLICATIONS

Lunner, K. D., et. al, (1988) Gene 74, 25–32.
Lee, C. C., et. al, (1988) Science 239, 1288–1291.
Xia, Y., et al, (1987) Nuc. Acids Res. 15(15), 6075–6090.
Zhang, Y., et. al, (1992) Nuc. Acids Res 20(20), 5351–5356.
Shields, S. L., et. al, (1990) Virology 126, 16–24.
Wilson, G. G. (1988) Gene 74, 281–289.
Dubey, et al., *Nucleic Acids Research* 20:1579–1585 (1992).
Brooks, et al., *Nucleic Acids Research* 19:841–850 (1991).
Howard, et al., *Nucleic Acids Research* 14:7939–7951 (1986).
Ito, et al., *Nucleic Acids Research* 18:3903–3911 (1990).
Kiss, et al., *Nucleic Acid Research* 13:6403–6421 (1985).
Nwanko, et al., *Gene* 64:1–8 (1988).
Rohozinski, et al, *Virology* 168:363–369 (1989).
Schuster, et al., *Virology* 150:170–177 (1986).
Slatko, et al., *Nucleic Acids Research* 15:9781–9796 (1987).
Van Etten, et al., *Nucleic Acids Res.* 13:3471–3478 (1985).
Bankier et al., *Methods in Enzymol.* 155:51–93 (1987).
Church and Gilbert, *Proc. Natl. Acad. Sci. USA* 81:1991–1995 (1984).
Davison, J. *DNA Sequencing and Mapping* 1:389–394 (1991).
Edwards et al., *Genomics* 6:593–608 (1990).
Gold et al., *Annu. Rev. Microbiol.* 35:365–403 (1981).
Karakashian et al., *Evolution* 19:368–377 (1965).
Kozak, *J. Cell. Biol.* 108:229 (1989).
Kozak, *Microbiol. Rev.* 47:1–45 (1983).
Lander et al., *Genomics* 2:231–239 (1988).
Mead et al., *Biotechniques* 11:76–87 (1991).
Messing, *Methods in Enzymol.* 101:20–78 (1983).
Miller et al., *Nucleic Acids Res.* 16:1215 (1988).
Nichols et al., *J. Phycol.* 1:34–38 (1965).
Thomas, *Prog. Nucl. Acid Res. Mol. Biol.* 5:315–337 (1966).

*Primary Examiner*—Charles L. Patterson, Jr.
*Attorney, Agent, or Firm*—Marshall, O'Toole, Gerstein, Murray & Borun

[57] ABSTRACT

DNA sequences encoding a novel restriction endonuclease (designated R.CviJI) and variants thereof are disclosed along with method and materials for production of the same by recombinant methods. A bacterial host cell line transformed with DNA encoding R.CviJI is also disclosed, as well as methods for expressing R.CviJI in the bacterial host system and subsequent materials and methods for purification of the enzyme.

11 Claims, 22 Drawing Sheets

FIGURE 2

| | 10 | 20 | 30 | 40 | 50 | 60 | |
|---|---|---|---|---|---|---|---|
| 1 | ATGTCTTTTC | GCACGTTAGA | ACTATTCGCC | GGTATAGAGTG | GTATTTCACA | TGGCCTCAGA | 60 |
| 61 | GGTATATCTA | CACCAGTTGC | ATTCGTAGAA | ATTAATGAAG | ACGCACACAA | ATTCTTGAAA | 120 |
| 121 | ACAAAGTTTT | CAGATGCATC | TGTATTCAAT | GACGTTACGA | AATTACCAA | ATCGGACTTC | 180 |
| 181 | CCAGAGAGACA | TAGACATGAT | TACTGCGGGA | TTCCCGTGCA | CTGGGTTTAG | TATTGCAGGT | 240 |
| 241 | TCTAGAACTG | GATTCGAACA | CAAGGAATCC | GGTCTCTTTG | CTGATGTGT | GCGAATCACG | 300 |
| 301 | GAAGAGTATA | AACCTAAAAT | AGTGTTTTG | GAAAACTTCC | ATATGTGTC | CCACACTTAC | 360 |
| 361 | AATCTCGATG | TCGTCGTAAA | AAAGATGGAT | GAAAATTGGTT | ATTTCTGCAA | GTGGGTAACT | 420 |
| 421 | TGCGGGGCAT | CAATTATAGG | AGCCCATCAT | CAACGCCACC | GGTGGTTTG | TCTCGCGATT | 480 |
| 481 | CGAAAAGATT | ATGAACCAGA | AGAAATAATT | GTATCTGTGA | ATGCTACAAA | GTTCGACTGG | 540 |
| 541 | GAAAATAATG | AACCACCGTG | TCAAGTAGAC | AATAAGAGTT | ACGAGAATTC | AACTCTTGTT | 600 |
| 601 | CGTCTCGGCAG | GATATTCCGT | GGTCCCCGAC | CAGATCAGAT | ATGCTTTCAC | CGGTCTATTT | 660 |
| 661 | ACAGGTGATT | TTGAGTCATC | GTGGAAAACT | ACCTTGACAC | CTGGGACAAT | AATTGGCACG | 720 |
| 721 | GAACACAAAA | AAATGAAAGG | AACTACGAT | AAGTCATAA | CTGGGTATTA | TGAGAACGAT | 780 |
| 781 | GTGTATTATT | CTTTTTCAAG | GAAAGAAGTT | CATCGCGCTC | CTCTAAATAT | ATCCGTGAAA | 840 |
| 841 | CCACGTGATA | TTCCGGAGAA | ACATAACGGA | AAAACACTCG | TAGATCGCGA | AATGATCAAG | 900 |
| 901 | AATATTGGT | GCACACATGC | TGCTAGTTAT | GGCACTGCTA | CTGCTGGATG | CAATGTTCTG | 960 |
| 961 | ACAGACCGTC | AGTCACATGC | ACTTCCTACA | CAAGTCAGGT | TTCATATATAG | GGGTGTATGT | 1020 |
| 1021 | GGACGACATT | TGTCTGGTAT | ATGGTGTGCA | TGGTTGATGG | GGTATGACCA | AGAATATCTT | 1080 |
| 1081 | GGTTATTGG | TTCAATATGA | TTAAAATATT | TGATACACT | AATGGGATAT | AAGAAGAAAA | 1140 |
| 1141 | CGTTTTACAA | TAGAAGGGGC | TAAACGTATA | ATACTCGAAA | AAAGAGAGACT | TGAAGAGAAA | 1200 |
| 1201 | AAAGAATTG | CGGAAGAGAA | AAAAAGAATT | GCACTTATAG | AAAAACAACG | AATTGCGGAA | 1260 |
| 1261 | GAGAAAAAA | GAATTGCGGA | AGAGAAAGAG | CGATTCGCAC | TTGAAGAGAA | AAACGAATT | 1320 |
| 1321 | GCGGAAGAAA | GAATTGCGGA | AGAGAAAGAG | CGCGGAAGAG | AAAAACGAA | GAAAAAAGA | 1380 |
| 1381 | CTTGCACTTA | TAGAAAAACA | ACGAATTGCG | GAAGAGAAAGAG | TTGCGTCGGG | GAGAAAAATT | 1440 |
| 1441 | AGAAAGAGGA | TCTCTACAAA | TGCAACAAAA | CATGAAAGAG | AATTTGTCAA | AGTTATAAAT | 1500 |

FIGURE 2 (CONTINUED)

```
1551 TCAATGTTCG TCGGACCCGC TACTTTTGTA TTCGTAGATA TAAAAGGTAA TAAATCCAGA 1560
1561 GAAATCCACA ACGTTGTAAG ATTCAGACAA TTACAAGGCA GTAAAGCGAA ATCCCCGACC 1620
1621 GCGTATGTTG ATAGAGAATA TAACAAACCT AAAGCGGATA TAGCAGCGGT AGACATAAAC 1680
1681 GGTAAAGATG TGGCATGGAT ATCCCATAAA GCATCTGAAG GATATCAACA ATATCTAAAA 1740
1741 ATTTCTGGAA AGAACCTCAA GTTCACAGGA AAAGAATTAG AAGAAGTTCT ATCGTTCAAG 1800
1801 AGAAAAGTAG TTAGTATGGC ACCGGTATCT CAAGCAATAT CTGCTAATAA GACCGTATGG 1860
1861 TCTCCTATCA AGTCAAATTT GATTAAAAAT CAAGCAATAT TCGGATTTGA TTACGGTAAG 1920
1921 AAACCAGGAA GGGACAATGT AGACATCATA GGTCAAGGAC GACCAATTAT AACAAAAAGA 1980
1981 GGTTCCATAT TATATCTTAC ATTCACTGGT TTTAGCGCAT TAAATGGGCA CTTGGAGAAT 2040
2041 TTTACTGGGA AACATGAACC CGTTTTCTAT GTAAGAACAG AACGGAGTAG TAGCGGGAGA 2100
2101 AGTATAACAA CTGTCGTCAA TGGTGTCACT TATAAAAATT TAAGATTCTT TATACATCCA 2160
2161 TACAACTTTG TTTCTTCAAA AACACAACGT ATTTGTCTA ACCATTTTCC CGAGAGACTT 2220
2221 TGTTGACCGC GTACTAAAAA ATGGTCACGA TATTTGTCTA AAGATGCTCA TAGAAGCAGG 2280
2281 TGCAAACCTT GACATCGTCA GTGTTGAGTA TACACCATTA CATCTACATG TGGTGATATT 2340
2341 TGTATAAACG GTAAATACCT ATATATACAA TACGTATCCC CCTAAAAGCG CTTAGATTTT 2400
2401 TTAGTTGTAT ACTACTTTTG TATAAGACCT GTAAGTTACA AACTAAAAGT TTCAGCTTTG 2460
2461 CCTTCGAAAC AAGCAATTAC CGCATGAGAA TAATATCCAT TATGGATGTT TTCTGCTAAT 2520
2521 AAAACGATAT TTCCTACAGA AGTTTCTATG ATTAGTTCCG AAATATTGAG ATCATCGTCA 2580
2580 CGTTTTCTT TACCGTATTT TACTTTCGTG ATCGTCGCAC CAATAAAATC ATCTCGTGTG 2640
2641 AGTTCATTCG GCAATTGTGC CGTGACACCA AATCTCTCAC CCACACCGTT ATGTCCATCC 2700
2701 ATTGCTAACA CTATCGGTAA CTATCGTGTG GTGTGTACGA TGTGAACTTC ATAACTATAA 2760
2761 CACGTGTAGT TGTCGTCTAT TCCATGTGTG TCGAGAGCGG TGTAAATAAA TTCAGATCTA 2820
2821 TTATTAATCG GATCTGATCC ATCATATAAC ATAAGAAGAA TCTTCATATT ATCATCCGAT 2880
2881 ATGTTCTGCA CACGAACAAC ATAAGAAGAA TACAAATAAA CATCTCTGAA 2940
2941 TCAACAAAAT CTTGCGAGTA TATAACATTA TATGATTGTT ACGAATCTC ACGTTTCATA 3000
3001 TCAACAAAAT ACATATATAC ACCATACAAA TATGATTGA CGTTAGTATA TAATGGATAA 3060
3061 CATTTGCAAT AGTATATTCA CTGCAGTAAA AAATGGCCAC GAAGCTTGTT TGAAGATGAT 3120
```

FIGURE 2 (CONTINUED)

```
3121  GCTCATTGAA AGAGGTAGCA ATATCAATGA TGTTTCCGAA TCAAAATATG GAAATACACC  3180
3181  ACTACATATT GCAGCTCATC ATGGTAATGA TGTGTGTTTG AAGATGCTTA TTGACGCAGG  3240
3241  TGCAAACCTT GATATCACAG ATATTTCTGG AGGAACACCA CTTCATCGTG CGGTTTTGAA  3300
3301  TGGCCATGAC ATATGTGTAC AGATGCTCGT AGAAGCAGGT GCAAACCTTA GTATCATAAC  3360
3361  TAATTTGGGA TGGATACCGT TACATTACGC GGCTTTTAAT GGTAATGATG CGATTTTGAG  3420
3421  GATGCTCATC GTTGTAAGTG ATAAATGTTGA CGTTATCAAT GATCGCGGTT GGACGGCGTT  3480
3481  ACATTACGCG GCTTTTAATG GTCATAGCAT GTGCGTCAAG ACGCTTATTG ATGCGGGTGC  3540
3541  AAATCTTGAC ATCACAGATA TTTCGGGATG TACACCACTT CATCGTGCGG TTTATAATGA  3600
3601  CCACGATGCA TGTGTGAAGA TACTCGTAGA AGCAGGTGCA ACTCTTGACG TCATTGATGA  3660
3661  TACTGAGTGG GTGCCGTTAC ATTACGCGGC TTTTAATGGT AATGATGCGA TTTTGAGGAT  3720
3721  GCTCATTGAA GCAGGTGCAG ATATTGATAT ACGATGTGTG CTCATCGAAG CGGGCGTTACA  3780
3781  TTACGCGGCT ATCACAGATA ACGATGTGTG TATAAAAACA ATTGCAGCAT CAGGTGGTAA  3840
3841  CATCAACGCC GTCAACAAAT CGGGGGATAC ACCACTAGAT GAGCGGCCGT GTCATGACAT  3900
3901  TGCAGTATGT GTGATCGTGA TAGTCAATAA GATCGTTTCG GATGTGTTGC TGCGTCCGAG  3960
3961  TGAGTTGTGT GTCATACCAC CAACGTCTGC TGCATTAGGT GATCACAGCG GAACGACGAT  4020
4021  GCGGCTTCAT GGGCGATCGG AAGCTGCAAA GATCACAGCG CATCTTCCTG TGGGTGCAAG  4080
4081  GGATACTCTA CGAAACTACTG CGTTGTGTTT GAACCGAACA ATTTCCGAGA GATCTCGTTG  4140
4141  ATAGTGTATT AATTGAATGC GTGTAAAGTT ACGCTATTTT TTCCAAAAAA GGGTTTGCAT  4200
4201  GAAATACAAC ACGATCTTT GTAGATCGTT TACCATTAGT TGTATTCGTG CAATAGAGAC  4260
4261  CATACGTACC TCCAAATTCA TTACTTTAC CTACAGTATT ACCACTTCCT TTTTTCCTA  4320
4321  TAGTAGTATC TAAATTCAAC CCTTTGAACT CATCGCCATT AACAGACAGA GCGTATGAAC  4380
4381  CGTTTGTGC CAATTTCACC TTCAAAAACGA CATGTAACCCA TTGACCTCTA GGAATTTTAA  4440
4441  CCGATCTTAT AAGTATCTGC TTACTTCCAA GTCCTTTTTC AAAAGCATAC AACGATCCTG  4500
4501  TAAGGTTATC CCCAGAACCT GAAATTGTAA GAAACGACTG GAAATGAATA GGTTGCATTA  4560
4561  GATCTGTATA CATATCACTT GGTTCGAAAT GTCCCAATTA TTCAGCACGA GCCTTGTAAG  4620
4621  ACCAAGTTTA ATACGGGGTC TTTCCACCGA GACCGGACAT TTCAGCACGA GCCTTGTAAG  4680
4681  AATGATATGA TGTGGTTAAA TCTCTATCAC CATCGTTCCA AACCGAAGAC  4740
```

FIGURE 2 (CONTINUED)

```
4741 CATGCATCGT TATACCTGGT GCAACCTGTA CTAAATTCTT TATTTCAGGT GCGGCTCCGG 4800
4801 GTGGATTAAC TCGAGATTCG TCAAATCTAA AATATGATAA CGATGTTCCA ACAGTAGAAC 4860
4861 CACTGGGTGG TATGGCAGTT GCTGGAAGGG AAGGTAAAAC TTAGGATAT TTCAAATCAC 4920
4921 CAACACCTTG AGGGTTTACT TGAATACTTC TGGGAGATGT TGGTGGTTTC GTCGAAGGTG 4980
4981 GTTTCGTTGA AGGTGGTTTC GTCGAAGGTG GTTTCGTCGA AGGTGGTTTC GTCGAAGGTG 5040
5041 GTTTCGTCGA AGGTGGTTTC GTCGAAGGTG GTTTCGTCGA AGGTGGTTTC GTCGAAGGTG 5100
5101 GTTTCGTCGA AGGTGGTTTC GTCGAAGGTG GTTTCGTCGA AGGTGGTTTC GTCGAAGGTG 5160
5161 GTTTCGTCGA AGGTGGTTTC GTCGAAGGTG GTTTCGTTGG CGGAAGTGGG GCATGACCAT 5220
5221 AATCCGTTAA ATTCCCGCAT TCACCTAATG TAAAGAACCG TAAAGAACCG GGTGCGCATT 5280
5281 GCATTCTTAT TGGTTCTGTA GTATCAGATA TACATACGAA ATAATGAGAA TCATTTTCCC 5340
5341 TGCCAAATAA TTTACCAGAT TTGCCTTTAC ATGACATTAT TTGTAATATA ATATTATTAT 5400
5401 AATTTTAAAA AAACTAACGT CTATTTAAAA ATGTAATAATA CGTATTATAT CAATGCATCA 5460
5461 TCTTAATCAT TTCCTAACGT ATAAGCGTAG CGAATTC                           5497
              |          |          |          |          |          |
              10         20         30         40         50         60
```

FIGURE 4

M.CviJI

```
  1  CAA GAA TAT CTT GGT TAT TTG GTT CAA TAT GAT TAA AATATTTGATACACTAA       5
      Q   E   Y   L   G   Y   L   V   Q   Y   D   *

55  ATG GAT ATA AGA AAG AGA CTT CGT TTT GAG AAA CTT ATA GAA GGG GCT AAA CGT ATA ATA    22
      M   D   I   R   K   R   L   R   F   E   K   L   I   E   G   A   K   R   I   I

106  CTC GAA AAA GCA CTT GAA ATA AAA TTT ACA AAA AAA CTT GAA AGA GAA GAG AAA AAA AGA    39
      L   E   K   A   L   E   I   K   F   T   K   K   L   E   R   E   E   K   K   R

157  AGA ATT GCA GAG CTT ATA AAA CGA TTC GAA CAA CGA GCA GAG GAA AAA AAA ATT GCG AGA    56
      R   I   A   E   L   I   K   R   F   E   Q   R   A   E   E   K   K   I   A   R

208  GCG GAA                                                                              73
      A   E

R.CviJI
259  GAA AAA GAA ATC GCG GAA GAG AAA AAA CGA ATC GAA ATC GAA GTG GAA GAG AAA AAA AAA     5
      E   K   E   I   A   E   E   K   K   R   I   E   I   E   V   E   E   K   K   K

310  AGA CTT GCA CTT ATA AGA CAA ATC TCT ATG CGA TCT TCT ACA AAT GCA GAA ATT GCG TCG    22
      R   L   A   L   I   R   Q   I   S   M   R   S   S   T   N   A   E   I   A   S

361  GGG AGA ATT AGA AAG GTT ATA TCA ATG TCA AGA AAA ATA TCA ACA CCC GCT GAG CAT GAA AGA    39
      G   R   I   R   K   V   I   S   M   S   R   K   I   S   T   P   A   E   H   E   R

412  GAA TTT GTC AAA ATA AAT AAT TCA AAA AAT AAA GGA ATC GTC GAA CCC GCT CAC ACT ACT GTT    56
      E   F   V   K   I   N   N   S   K   N   K   G   I   V   E   P   A   H   T   T   V

463  TTC AGA CAA TTA CAA AGT GGC AAA AGC GCG ACC TAT GCG TAT GTT GAT                      73
      F   R   Q   L   Q   S   G   K   S   A   T   Y   A   Y   V   D

514  TTC GTA GAT CAA TTA CAA AGT GGC AGT AAA GCG AAA TCC ACC TAT GCG TAT GTT GAT          90
      F   V   D   Q   L   Q   S   G   S   K   A   K   S   T   Y   A   Y   V   D

565  AGA GAA TAT AAC AAC CCT AAA AAA GCG GAT ATA GCA GCG GTA GAC ATA ACC GGT              107
      R   E   Y   N   N   P   K   K   A   D   I   A   A   V   D   I   T   G
```

FIGURE 4 (CONTINUED)

```
 616  AAA GAT GTG GCA TGG ATA TCC CAT AAA GCA TCT GAA GGA TAT CAA CAA TAT  124
       K   D   V   A   W   I   S   H   K   A   S   E   G   Y   Q   Q   Y
 667  CTA AAA ATT TCT GGA AAG AAC CTC AAG TTC ACA GGA AAA GAA TTA GAA GAA  141
       L   K   I   S   G   K   N   L   K   F   T   G   K   E   L   E   E
 718  GTT CTA TCG TTC AAG AGA GTA AAA GTT AGT GTT GCA CCG GTA TCT AAA ATA  158
       V   L   S   F   K   R   V   K   V   S   V   A   P   V   S   K   I
 769  TGG CCT GCT AAT ATA ACC AAG ATC ATG TCT CCT TTG AGG AGG TCA ATT AAA  175
       W   P   A   N   I   T   K   I   M   S   P   L   R   R   S   I   K
 820  AAT CAA GCA ATA ATA GGA GTA TCA TAT AAG AAA ATA GGA CCA TCC GAC AAT  192
       N   Q   A   I   I   G   V   S   Y   K   K   I   G   P   S   D   N
 871  GTA GAC ATC ATA CTT CAA CGA TTT GAT CGA CCA ATA AAA AGA GGG CAC ATA  209
       V   D   I   I   L   Q   R   F   D   R   P   I   K   R   G   H   I
 922  TTA TAT ACA GGG TTC ACT AGC GCA TTA AAT GGT GGT TTG GAG AGT TTA  226
       L   Y   T   G   F   T   S   A   L   N   G   G   V   L   E   S   L
 973  TTT ACT GGG AGA AGT ATA TAT GTA AAT CGG TAT AAA CGG TAT AAA AAT AGT  243
       F   T   G   R   S   I   Y   V   N   R   Y   T   Y   K   N   S
1024  AGC GGG TTC ATA AGT AAA CAT CCC GAA ACA CCA AAT GGT GTC ACT TAT ATT  260
       S   G   F   I   S   K   H   P   E   T   P   N   G   V   T   Y   I
1075  AGA TAG TTC ATA CAT CCA TAC TTT GTT AAC AAT GTT CA TCA AAA ACA CAA TTA  277
       R   F   I   H   P   Y   F   V   N   N   F   S   K   T   Q   L
1126  ATG TAG GAC CAT TTT CCC GAG AGA CTT TGT TGA CCG GCG TAC TAA AAA ATG GTC ACG ATA TTT GTC  278
       M
1191  TAA AGA TGC TCA TAG AAG CAG GTG CAA ACC TTG AC
```

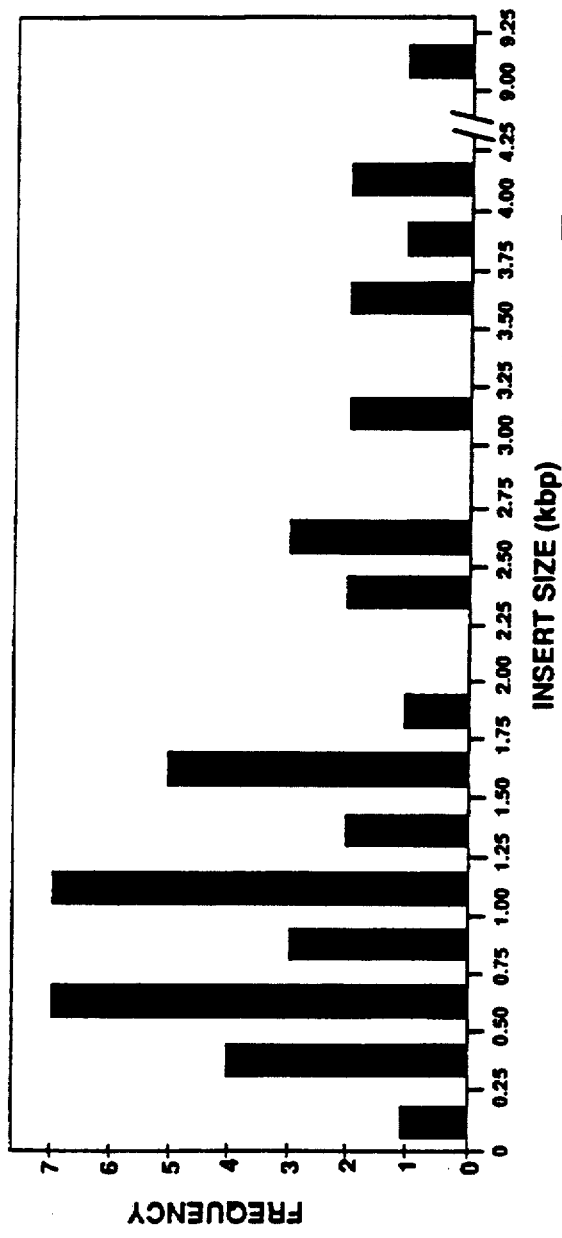
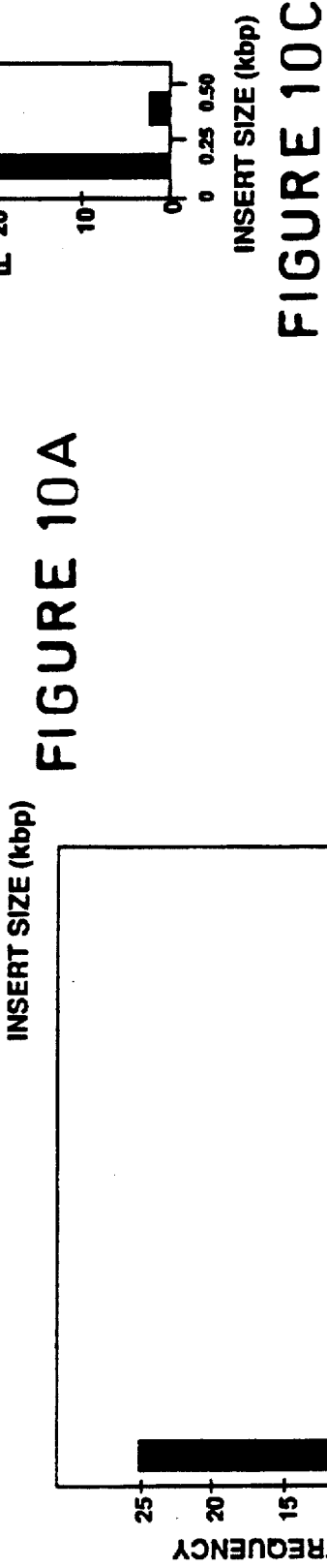
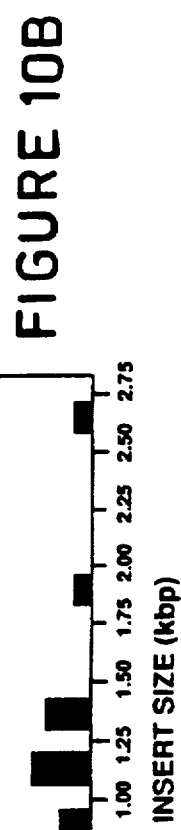
FIGURE 10A
FIGURE 10B
FIGURE 10C

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

CAATTTCACA CAGGAAACAG CTATGTCTTT TCGCACGTTA GAAC 44

( 2 ) INFORMATION FOR SEQ ID NO:2:

( i ) SEQUENCE CHARACTERISTICS:
( A ) LENGTH: 5496 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| ATGTCTTTTC | GCACGTTAGA | ACTATTCGCC | GGTATAGCTG | GTATTTCACA | TGGCCTCAGA | 60 |
| GGTATATCTA | CACCAGTTGC | ATTCGTAGAA | ATTAATGAAG | ACGCACAAAA | ATTCTTGAAA | 120 |
| ACAAAGTTTT | CAGATGCATC | TGTATTCAAT | GACGTTACGA | AATTTACCAA | ATCGGACTTC | 180 |
| CCAGAAGACA | TAGACATGAT | TACTGCGGGA | TTCCCGTGCA | CTGGGTTTAG | TATTGCAGGT | 240 |
| TCTAGAACTG | GATTCGAACA | CAAGGAATCC | GGTCTCTTTG | CTGATGTTGT | GCGAATCACG | 300 |
| GAAGAGTATA | AACCTAAAAT | AGTGTTTTTG | GAAAACTCCC | ATATGTTGTC | CCACACTTAC | 360 |
| AATCTCGATG | TCGTCGTAAA | AAGATGGAT | GAAATTGGTT | ATTTCTGCAA | GTGGGTAACT | 420 |
| TGTCGGGCAT | CAATTATAGG | AGCCCATCAT | CAACGCCACC | GGTGGTTTTG | TCTCGCGATT | 480 |
| CGAAAAGATT | ATGAACCAGA | AGAAATAATT | GTATCTGTGA | ATGCTACAAA | GTTCGACTGG | 540 |
| GAAAATAATG | AACCACCGTG | TCAAGTAGAC | AATAAGAGTT | ACGAGAATTC | AACTCTTGTT | 600 |
| CGTCTGGCAG | GATATTCCGT | GGTCCCCGAC | CAGATCAGAT | ATGCTTTCAC | CGGTCTATTT | 660 |
| ACAGGTGATT | TTGAGTCATC | GTGGAAAACT | ACCTTGACAC | CTGGGACAAT | AATTGGCACG | 720 |
| GAACACAAAA | AAATGAAAGG | AACTTACGAT | AAAGTCATAA | ACGGGTATTA | TGAGAACGAT | 780 |
| GTGTATTATT | CTTTTTCAAG | GAAAGAAGTT | CATCGCGCTC | CTCTAAATAT | ATCCGTGAAA | 840 |
| CCACGTGATA | TTCCGGAGAA | ACATAACGGA | AAAACACTCG | TAGATCGCGA | AATGATCAAG | 900 |
| AAATATTGGT | GCACACCATG | TGCTAGTTAT | GGCACTGCTA | CTGCTGGATG | CAATGTTCTG | 960 |
| ACAGACCGTC | AGTCACATGC | ACTTCCTACA | CAAGTCAGGT | TTCATATAG | GGTGTATGT | 1020 |
| GGACGACATT | TGTCTGGTAT | ATGGTGTGCA | TGGTTGATGG | GGTATGACCA | AGAATATCTT | 1080 |
| GGTTATTTGG | TTCAATATGA | TTAAAATATT | TTGATACACT | AAATGGATAT | AAGAAGAAAA | 1140 |
| CGTTTTACAA | TAGAAGGGGC | TAAACGTATA | ATACTCGAAA | AAAAGAGACT | TGAAGAGAAA | 1200 |
| AAAAGAATTG | CGGAAGAGAA | AAAAAGAATT | GCACTTATAG | AAAAACAACG | AATTGCGGAA | 1260 |
| GAGAAAAAAA | GAATTGCGGA | AGAGAAAAAA | CGATTCGCAC | TTGAAGAGAA | AAAACGAATT | 1320 |
| GCGGAAGAAA | AAAACGAAT | CGCGGAAGAG | AAAAAACGAA | TCGTGGAAGA | GAAAAAAAGA | 1380 |
| CTTGCACTTA | TAGAAAAACA | ACGAATTGCG | GAAGAGAAAA | TTGCGTCGGG | GAGAAAAATT | 1440 |
| AGAAAGAGGA | TCTCTACAAA | TGCAACAAAA | CATGAAAGAG | AATTTGTCAA | AGTTATAAAT | 1500 |
| TCAATGTTCG | TCGGACCCGC | TACTTTTGTA | TTCGTAGATA | TAAAAGGTAA | TAAATCCAGA | 1560 |
| GAAATCCACA | ACGTTGTAAG | ATTCAGACAA | TTACAAGGCA | GTAAAGCGAA | ATCCCCGACC | 1620 |
| GCGTATGTTG | ATAGAGAATA | TAACAAACCT | AAAGCGGATA | TAGCAGCGGT | AGACATAACC | 1680 |
| GGTAAAGATG | TGGCATGGAT | ATCCCATAAA | GCATCTGAAG | GATATCAACA | ATATCTAAAA | 1740 |
| ATTTCTGGAA | AGAACCTCAA | GTTCACAGGA | AAAGAATTAG | AAGAAGTTCT | ATCGTTCAAG | 1800 |

```
AGAAAAGTAG TTAGTATGGC ACCGGTATCT AAAATATGGC CTGCTAATAA GACCGTATGG    1860
TCTCCTATCA AGTCAAATTT GATTAAAAAT CAAGCAATAT TCGGATTTGA TTACGGTAAG    1920
AAACCAGGAA GGGACAATGT AGACATCATA GGTCAAGGAC GACCAATTAT AACAAAAGA     1980
GGTTCCATAT TATATCTTAC ATTCACTGGT TTTAGCGCAT TAAATGGGCA CTTGGAGAAT    2040
TTTACTGGGA AACATGAACC CGTTTTCTAT GTAAGAACAG AACGGAGTAG TAGCGGGAGA    2100
AGTATAACAA CTGTCGTCAA TGGTGTCACT TATAAAAATT TAAGATTCTT TATACATCCA    2160
TACAACTTTG TTTCTTCAAA AACACAACGT ATTATGTAGG ACCATTTCC CGAGAGACTT     2220
TGTTGACCGC GTACTAAAAA ATGGTCACGA TATTTGTCTA AAGATGCTCA TAGAAGCAGG    2280
TGCAAACCTT GACATCGTCA GTGTTGAGTA TACACCATTA CATCTACATG TGGTGATATT    2340
TGTATAAACG GTAAATACCT ATATATACAA TACGTATCCC CCTAAAAGCG CTTAGATTTT    2400
TTAGTTGTAT ACTACTTTTG TATAAGACCT GTAAGTTACA AACTAAAAGT TTCAGCTTTG    2460
CCTTCGAAAC AAGCAATTAC CGCATGAGAA TAATATCCAT TATGGATGTT TTCTGCTAAT    2520
AAAACGATAT TTCCTACAGA AGTTTCTATG ATTAGTTCCG AAATATTGAG ATCATCGTCA    2580
CGTTTTCTT TACCGTATTT TACTTTCGTG ATCGTCGCAC CAATAAAATC ATCTCGTGTG     2640
AGTTCATTCG GCAATTGTGC CGTGACACCA AATCTCTCAC AACAACCTTG ATGTCCATCC    2700
ATTGCTAACA CTATCGGTAA TCCATGTGTG GTGTGTACGA CCACACCGTT ATAACTATAA    2760
CACGTGTAGT TGTCGTCTAT ATCATATAAC TCGAGAGCGG TGTGAACTTC TTCAGATCTA    2820
TTATTAATCG GATCTGATCC ATAAGAAGAA TCTTCATATT TACAAATAAA ATCATCCGAT    2880
ATGTTCTGCA CACGAACAAC ATTCGTCAAA TTTCTGTGAT GACGAATCTC CATCTCTGAA    2940
TCATTAGAGA CTTGCGAGTA TATAACATTA TAATTGTTGA TATGATTATT ACGTTTCATA    3000
TCAACAAAAT ACATATAAAC ACCATACAAA TATTAAAACA CGTTAGTATA TAATGGATAA    3060
CATTTGCAAT AGTATATTCA CTGCAGTAAA AAATGGCCAC GAAGCTTGTT TGAAGATGAT    3120
GCTCATTGAA AGAGGTAGCA ATATCAATGA TGTTTCCGAA TCAAAATATG GAAATACACC    3180
ACTACATATT GCAGCTCATC ATGGTAATGA TGTGTGTTTG AAGATGCTTA TTGACGCAGG    3240
TGCAAACCTT GATATCACAG ATATTTCTGG AGGAACACCA CTTCATCGTG CGGTTTTGAA    3300
TGGCCATGAC ATATTGTACA GATGCTCGTA GAAGCAGGTG CAAACCTTAG TATCATAACT    3360
AATTTGGGAT GGATACCGTT ACATTACGCG GCTTTTAATG GTAATGATGC GATTTTGAGG    3420
ATGCTCATCG TTGTAAGTGA TAATGTTGAC GTTATCAATG ATCGCGGTTG GACGGCGTTA    3480
CATTACGCGG CTTTTAATGG TCATAGCATG TGCGTCAAGA CGCTTATTGA TGCGGGTGCA    3540
AATCTTGACA TCACAGATAT TTCGGGATGT ACACCACTTC ATCGTGCGGT TTATAATGAC    3600
CACGATGCAT GTGTGAAGAT ACTCGTAGAA GCAGGTGCAA CTCTTGACGT CATTGATGAT    3660
ACTGAGTGGG TGCCGTTACA TTACGCGGCT TTAATGGTA ATGATGCGAT TTTGAGGATG     3720
CTCATTGAAG CAGGTGCAGA TATTGATATA TCTAATATAT GTGATTGGAC GGCGTTACAT    3780
TACGCGGCTC GAAATGGACA CGATGTGTGT ATAAAACAC TCATCGAAGC AGGTGGTAAC     3840
ATCAACGCCG TCAACAAATC GGGGGATACA CCACTAGATA TTGCAGCATG TCATGACATT    3900
GCAGTATGTG TGATCGTGAT AGTCAATAAG ATCGTTTCGG AGCGGCCGTT GCGTCCGAGT    3960
GAGTTGTGTG TCATACCACC AACGTCTGCT GCATTAGGTG ATGTGTTGCG AACGACGATG    4020
CGGCTTCATG GGCGATCGGA AGCTGCAAAG ATCACAGCGC ATCTTCCTGT GGGTGCAAGG    4080
GATACTCTAC GAACTACTGC GTTGTGTTTG AACCGAACAA TTTCCGAGAG ATCTCGTTGA    4140
TAGTGTATTA ATTGAATGCG TGTAAAGTTA CGCTATTTTT TTCCAAAAAG GGTTTGCATG    4200
```

-continued

```
AAATACAACA CGATCTTTTG TAGATCGTTT ACCATTAGTT GTATTCGTGC AATAGAGACC    4260
ATACGTACCT CCAAATTCAT TTACTTTACC TACAGTATTA CCACTTCCTT TTTTTCCTAT    4320
AGTAGTATCT AAATTCAACC CTTTGAACTC ATCGCCATTA ACAGACAGAG CGTATGAACC    4380
GTTTTGTGCC AATTTCACCT TCAAAACGAT AGTAACCCAT TGACCTCTAG GAATTTTAAC    4440
CGATCTTATA AGTATCTGCT TACTTCCAAG TCCTTTTTCA AAAGCATACA ACGATCCTGT    4500
AAGGTTATCC CCAGAACCTG AAATTGTAAA GAACGACTGG AAATGAATAG GTTGCATTAG    4560
ATCTGTATAC ATATCACTTG GTTCGAAATG AAAATCGTAG TCCCAATTAG GTACGTTCCA    4620
CCAAGTTTAA TACGGGGTCT TTCCACCGAG ACCGGACATT TCAGCACGAG CCTTGTAAGA    4680
ATGATATGAT GTGGTTAAAT CTCTATCACC ATCGTTCCAC TTTCCTCTGA ACCGAAGACC    4740
ATGCATCGTT ATACCTGGTG CAACCTGTAC TAAATTCTTT ATTTCAGGTG CGGCTCCGGG    4800
TGGATTAACT CGAGATTCGT CAAATCTAAA ATATGATAAC GATGTTCCAA CAGTAGAACC    4860
ACTGGGTGGT ATGGCAGTTG CTGGAAGGGA AGGTAAAACT TTAGGATATT TCAAATCACC    4920
AACACCTTGA GGGTTTACTT GAATACTTCT GGGAGATGTT GGTGGTTTCG TCGAAGGTGG    4980
TTTCGTTGAA GGTGGTTTCG TCGAAGGTGG TTTCGTCGAA GGTGGTTTCG TCGAAGGTGG    5040
TTTCGTCGAA GGTGGTTTCG TCGAAGGTGG TTTCGTCGAA GGTGGTTTCG TCGAAGGTGG    5100
TTTCGTCGAA GGTGGTTTCG TCGAAGGTGG TTTCGTCGAA GGTGGTTTCG TCGAAGGTGG    5160
TTTCGTCGAA GGTGGTTTCG TCGAAGGTGG TTTCGTTGGC GGAAGTGGGG CATGACCATA    5220
ATCCGTTAAA TTCCCGCATT CACCTAATGA TGTACTCCAT AAAGAACCGG GTGCGCATTG    5280
CATTCTTATT GGTTCTGTAG TATCAGATAT ACATACGAAA TAATGAGAAT CATTTTCCCT    5340
GCCAAATAAT TTACCAGATT TGCCTTTACA TGACATTATT TGTAATATAA TATTATTATA    5400
ATTTTAAAAA AACTAACGTC TATTTAAAAT TATGTAATAC GTATTATATC AATGCATCAT    5460
CTTAATCATT TCCTAACGTA TAAGCGTAGC GAATTC                              5496
```

( 2 ) INFORMATION FOR SEQ ID NO:3:

( i ) SEQUENCE CHARACTERISTICS:
        ( A ) LENGTH: 1225 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(1..33, 55..1128)

( x i ) SEQUENCE DESCRIPTION: SEQ ID NO:3:

```
CAA GAA TAT CTT GGT TAT TTG GTT CAA TAT GAT TAAAATATTT TGATACACTA      53
Gln Glu Tyr Leu Gly Tyr Leu Val Gln Tyr Asp
  1               5                  10

A ATG GAT ATA AGA AGA AAA CGT TTT ACA ATA GAA GGG GCT AAA CGT          99
  Met Asp Ile Arg Arg Lys Arg Phe Thr Ile Glu Gly Ala Lys Arg
      15                  20                  25

ATA ATA CTC GAA AAA AAG AGA CTT GAA GAG AAA AAA AGA ATT GCG GAA       147
Ile Ile Leu Glu Lys Lys Arg Leu Glu Glu Lys Lys Arg Ile Ala Glu
            30                  35                  40

GAG AAA AAA AGA ATT GCA CTT ATA GAA AAA CAA CGA ATT GCG GAA GAG       195
Glu Lys Lys Arg Ile Ala Leu Ile Glu Lys Gln Arg Ile Ala Glu Glu
        45                  50                  55

AAA AAA AGA ATT GCG GAA GAG AAA AAA CGA TTC GCA CTT GAA GAG AAA       243
```

|  |  |  |  |  |  |  |  |  |  |  |  |  |  |  |  |  |
|---|---|---|---|---|---|---|---|---|---|---|---|---|---|---|---|---|
| Lys | Lys | Arg | Ile | Ala | Glu | Glu | Lys | Lys | Arg | Phe | Ala | Leu | Glu | Glu | Lys |  |
|  | 60 |  |  |  | 65 |  |  |  | 70 |  |  |  |  |  |  |  |

| AAA | CGA | ATT | GCG | GAA | GAA | AAA | AAA | CGA | ATC | GCG | GAA | GAG | AAA | AAA | CGA | 291 |
|---|---|---|---|---|---|---|---|---|---|---|---|---|---|---|---|---|
| Lys | Arg | Ile | Ala | Glu | Glu | Lys | Lys | Arg | Ile | Ala | Glu | Glu | Lys | Lys | Arg |  |
| 75 |  |  |  | 80 |  |  |  | 85 |  |  |  |  |  |  | 90 |  |

| ATC | GTG | GAA | GAG | AAA | AAA | AGA | CTT | GCA | CTT | ATA | GAA | AAA | CAA | CGA | ATT | 339 |
|---|---|---|---|---|---|---|---|---|---|---|---|---|---|---|---|---|
| Ile | Val | Glu | Glu | Lys | Lys | Arg | Leu | Ala | Leu | Ile | Glu | Lys | Gln | Arg | Ile |  |
|  |  |  |  | 95 |  |  |  | 100 |  |  |  |  | 105 |  |  |  |

| GCG | GAA | GAG | AAA | ATT | GCG | TCG | GGG | AGA | AAA | ATT | AGA | AAG | AGG | ATC | TCT | 387 |
|---|---|---|---|---|---|---|---|---|---|---|---|---|---|---|---|---|
| Ala | Glu | Glu | Lys | Ile | Ala | Ser | Gly | Arg | Lys | Ile | Arg | Lys | Arg | Ile | Ser |  |
|  |  |  | 110 |  |  |  | 115 |  |  |  |  | 120 |  |  |  |  |

| ACA | AAT | GCA | ACA | AAA | CAT | GAA | AGA | GAA | TTT | GTC | AAA | GTT | ATA | AAT | TCA | 435 |
|---|---|---|---|---|---|---|---|---|---|---|---|---|---|---|---|---|
| Thr | Asn | Ala | Thr | Lys | His | Glu | Arg | Glu | Phe | Val | Lys | Val | Ile | Asn | Ser |  |
|  |  | 125 |  |  |  |  | 130 |  |  |  |  | 135 |  |  |  |  |

| ATG | TTC | GTC | GGA | CCC | GCT | ACT | TTT | GTA | TTC | GTA | GAT | ATA | AAA | GGT | AAT | 483 |
|---|---|---|---|---|---|---|---|---|---|---|---|---|---|---|---|---|
| Met | Phe | Val | Gly | Pro | Ala | Thr | Phe | Val | Phe | Val | Asp | Ile | Lys | Gly | Asn |  |
|  | 140 |  |  |  |  | 145 |  |  |  |  | 150 |  |  |  |  |  |

| AAA | TCC | AGA | GAA | ATC | CAC | AAC | GTT | GTA | AGA | TTC | AGA | CAA | TTA | CAA | GGC | 531 |
|---|---|---|---|---|---|---|---|---|---|---|---|---|---|---|---|---|
| Lys | Ser | Arg | Glu | Ile | His | Asn | Val | Val | Arg | Phe | Arg | Gln | Leu | Gln | Gly |  |
| 155 |  |  |  |  | 160 |  |  |  |  | 165 |  |  |  |  | 170 |  |

| AGT | AAA | GCG | AAA | TCC | CCG | ACC | GCG | TAT | GTT | GAT | AGA | GAA | TAT | AAC | AAA | 579 |
|---|---|---|---|---|---|---|---|---|---|---|---|---|---|---|---|---|
| Ser | Lys | Ala | Lys | Ser | Pro | Thr | Ala | Tyr | Val | Asp | Arg | Glu | Tyr | Asn | Lys |  |
|  |  |  |  | 175 |  |  |  |  | 180 |  |  |  |  | 185 |  |  |

| CCT | AAA | GCG | GAT | ATA | GCA | GCG | GTA | GAC | ATA | ACC | GGT | AAA | GAT | GTG | GCA | 627 |
|---|---|---|---|---|---|---|---|---|---|---|---|---|---|---|---|---|
| Pro | Lys | Ala | Asp | Ile | Ala | Ala | Val | Asp | Ile | Thr | Gly | Lys | Asp | Val | Ala |  |
|  |  |  | 190 |  |  |  |  | 195 |  |  |  |  | 200 |  |  |  |

| TGG | ATA | TCC | CAT | AAA | GCA | TCT | GAA | GGA | TAT | CAA | CAA | TAT | CTA | AAA | ATT | 675 |
|---|---|---|---|---|---|---|---|---|---|---|---|---|---|---|---|---|
| Trp | Ile | Ser | His | Lys | Ala | Ser | Glu | Gly | Tyr | Gln | Gln | Tyr | Leu | Lys | Ile |  |
|  |  | 205 |  |  |  |  | 210 |  |  |  |  | 215 |  |  |  |  |

| TCT | GGA | AAG | AAC | CTC | AAG | TTC | ACA | GGA | AAA | GAA | TTA | GAA | GAA | GTT | CTA | 723 |
|---|---|---|---|---|---|---|---|---|---|---|---|---|---|---|---|---|
| Ser | Gly | Lys | Asn | Leu | Lys | Phe | Thr | Gly | Lys | Glu | Leu | Glu | Glu | Val | Leu |  |
|  | 220 |  |  |  |  | 225 |  |  |  |  | 230 |  |  |  |  |  |

| TCG | TTC | AAG | AGA | AAA | GTA | GTT | AGT | ATG | GCA | CCG | GTA | TCT | AAA | ATA | TGG | 771 |
|---|---|---|---|---|---|---|---|---|---|---|---|---|---|---|---|---|
| Ser | Phe | Lys | Arg | Lys | Val | Val | Ser | Met | Ala | Pro | Val | Ser | Lys | Ile | Trp |  |
| 235 |  |  |  |  | 240 |  |  |  |  | 245 |  |  |  |  | 250 |  |

| CCT | GCT | AAT | AAG | ACC | GTA | TGG | TCT | CCT | ATC | AAG | TCA | AAT | TTG | ATT | AAA | 819 |
|---|---|---|---|---|---|---|---|---|---|---|---|---|---|---|---|---|
| Pro | Ala | Asn | Lys | Thr | Val | Trp | Ser | Pro | Ile | Lys | Ser | Asn | Leu | Ile | Lys |  |
|  |  |  |  | 255 |  |  |  |  | 260 |  |  |  |  | 265 |  |  |

| AAT | CAA | GCA | ATA | TTC | GGA | TTT | GAT | TAC | GGT | AAG | AAA | CCA | GGA | AGG | GAC | 867 |
|---|---|---|---|---|---|---|---|---|---|---|---|---|---|---|---|---|
| Asn | Gln | Ala | Ile | Phe | Gly | Phe | Asp | Tyr | Gly | Lys | Lys | Pro | Gly | Arg | Asp |  |
|  |  |  | 270 |  |  |  |  | 275 |  |  |  |  | 280 |  |  |  |

| AAT | GTA | GAC | ATC | ATA | GGT | CAA | GGA | CGA | CCA | ATT | ATA | ACA | AAA | AGA | GGT | 915 |
|---|---|---|---|---|---|---|---|---|---|---|---|---|---|---|---|---|
| Asn | Val | Asp | Ile | Ile | Gly | Gln | Gly | Arg | Pro | Ile | Ile | Thr | Lys | Arg | Gly |  |
|  |  | 285 |  |  |  |  | 290 |  |  |  |  | 295 |  |  |  |  |

| TCC | ATA | TTA | TAT | CTT | ACA | TTC | ACT | GGT | TTT | AGC | GCA | TTA | AAT | GGG | CAC | 963 |
|---|---|---|---|---|---|---|---|---|---|---|---|---|---|---|---|---|
| Ser | Ile | Leu | Tyr | Leu | Thr | Phe | Thr | Gly | Phe | Ser | Ala | Leu | Asn | Gly | His |  |
|  | 300 |  |  |  |  | 305 |  |  |  |  | 310 |  |  |  |  |  |

| TTG | GAG | AAT | TTT | ACT | GGG | AAA | CAT | GAA | CCC | GTT | TTC | TAT | GTA | AGA | ACA | 1011 |
|---|---|---|---|---|---|---|---|---|---|---|---|---|---|---|---|---|
| Leu | Glu | Asn | Phe | Thr | Gly | Lys | His | Glu | Pro | Val | Phe | Tyr | Val | Arg | Thr |  |
| 315 |  |  |  |  | 320 |  |  |  |  | 325 |  |  |  |  | 330 |  |

| GAA | CGG | AGT | AGT | AGC | GGG | AGA | AGT | ATA | ACA | ACT | GTC | GTC | AAT | GGT | GTC | 1059 |
|---|---|---|---|---|---|---|---|---|---|---|---|---|---|---|---|---|
| Glu | Arg | Ser | Ser | Ser | Gly | Arg | Ser | Ile | Thr | Thr | Val | Val | Asn | Gly | Val |  |
|  |  |  | 335 |  |  |  |  | 340 |  |  |  |  | 345 |  |  |  |

| ACT | TAT | AAA | AAT | TTA | AGA | TTC | TTT | ATA | CAT | CCA | TAC | AAC | TTT | GTT | TCT | 1107 |
|---|---|---|---|---|---|---|---|---|---|---|---|---|---|---|---|---|
| Thr | Tyr | Lys | Asn | Leu | Arg | Phe | Phe | Ile | His | Pro | Tyr | Asn | Phe | Val | Ser |  |
|  |  |  | 350 |  |  |  |  | 355 |  |  |  |  | 360 |  |  |  |

| TCA | AAA | ACA | CAA | CGT | ATT | ATG | TAGGACCATT | TTCCCGAGAG | ACTTTGTTGA | 1158 |
|---|---|---|---|---|---|---|---|---|---|---|
| Ser | Lys | Thr | Gln | Arg | Ile | Met |  |  |  |  |
|  |  | 365 |  |  |  |  |  |  |  |  |

-continued

```
CCGCGTACTA AAAAATGGTC ACGATATTTG TCTAAAGATG CTCATAGAAG CAGGTGCAAA    1218
CCTTGAC                                                               1225
```

( 2 ) INFORMATION FOR SEQ ID NO:4:

( i ) SEQUENCE CHARACTERISTICS:
        ( A ) LENGTH: 369 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Gln Glu Tyr Leu Gly Tyr Leu Val Gln Tyr Asp Met Asp Ile Arg Arg
  1           5                  10                  15
Lys Arg Phe Thr Ile Glu Gly Ala Lys Arg Ile Ile Leu Glu Lys Lys
             20                  25                  30
Arg Leu Glu Glu Lys Lys Arg Ile Ala Glu Glu Lys Lys Arg Ile Ala
             35                  40                  45
Leu Ile Glu Lys Gln Arg Ile Ala Glu Glu Lys Lys Arg Ile Ala Glu
         50                  55                  60
Glu Lys Lys Arg Phe Ala Leu Glu Glu Lys Lys Arg Ile Ala Glu Glu
 65                  70                  75                  80
Lys Lys Arg Ile Ala Glu Glu Lys Lys Arg Ile Val Glu Glu Lys Lys
                 85                  90                  95
Arg Leu Ala Leu Ile Glu Lys Gln Arg Ile Ala Glu Glu Lys Ile Ala
            100                 105                 110
Ser Gly Arg Lys Ile Arg Lys Arg Ile Ser Thr Asn Ala Thr Lys His
            115                 120                 125
Glu Arg Glu Phe Val Lys Val Ile Asn Ser Met Phe Val Gly Pro Ala
    130                 135                 140
Thr Phe Val Phe Val Asp Ile Lys Gly Asn Lys Ser Arg Glu Ile His
145                 150                 155                 160
Asn Val Val Arg Phe Arg Gln Leu Gln Gly Ser Lys Ala Lys Ser Pro
                165                 170                 175
Thr Ala Tyr Val Asp Arg Glu Tyr Asn Lys Pro Lys Ala Asp Ile Ala
            180                 185                 190
Ala Val Asp Ile Thr Gly Lys Asp Val Ala Trp Ile Ser His Lys Ala
        195                 200                 205
Ser Glu Gly Tyr Gln Gln Tyr Leu Lys Ile Ser Gly Lys Asn Leu Lys
    210                 215                 220
Phe Thr Gly Lys Glu Leu Glu Glu Val Leu Ser Phe Lys Arg Lys Val
225                 230                 235                 240
Val Ser Met Ala Pro Val Ser Lys Ile Trp Pro Ala Asn Lys Thr Val
                245                 250                 255
Trp Ser Pro Ile Lys Ser Asn Leu Ile Lys Asn Gln Ala Ile Phe Gly
            260                 265                 270
Phe Asp Tyr Gly Lys Lys Pro Gly Arg Asp Asn Val Asp Ile Ile Gly
        275                 280                 285
Gln Gly Arg Pro Ile Ile Thr Lys Arg Gly Ser Ile Leu Tyr Leu Thr
    290                 295                 300
Phe Thr Gly Phe Ser Ala Leu Asn Gly His Leu Glu Asn Phe Thr Gly
305                 310                 315                 320
Lys His Glu Pro Val Phe Tyr Val Arg Thr Glu Arg Ser Ser Ser Gly
                325                 330                 335
```

| Arg | Ser | Ile | Thr | Thr | Val | Val | Asn | Gly | Val | Thr | Tyr | Lys | Asn | Leu | Arg |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Phe | Phe | Ile | His | Pro | Tyr | Asn | Phe | Val | Ser | Ser | Lys | Thr | Gln | Arg | Ile |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

Met ( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

GTAAAACGAC GGCCAGT　　　　　　　　　　　　　　　　　　　　　　　　　　　17

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

GCCAAGCTTG GATGAT　　　　　　　　　　　　　　　　　　　　　　　　　　　16

( 2 ) INFORMATION FOR SEQ ID NO:7:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

ATCTTCGCGA ATTCACTGGC CGTCGTTTTA C　　　　　　　　　　　　　　　31

( 2 ) INFORMATION FOR SEQ ID NO:8:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GAATTCGCGA AGAT　　　　　　　　　　　　　　　　　　　　　　　　　　　14

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

ATCATCCAAG CTTGGCACTG GCCGTCGTTT TAC    33

( 2 ) INFORMATION FOR SEQ ID NO:10:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GTAAAACGAC GGCCAGTGAA TTCGCGAAGA TNNNNNNNN NNNNNNNAT CATCCAAGCT    60

TGGCACTGGC CGTCGTTTTA C    81

( 2 ) INFORMATION FOR SEQ ID NO:11:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

GTAAAACGAC GGCCAGTGCC AAGCTTGGAT GATNNNNNNN NNNNNNNNN ATCTTCGCGA    60

ATTCACTGGC CGTCGTTTTA C    81

( 2 ) INFORMATION FOR SEQ ID NO:12:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(26..148, 190..207, 244..270)

( x i ) SEQUENCE DESCRIPTION: SEQ ID NO:12:

```
TAACAATTTC ACACAGGAAA CAGCT ATG ACC ATG ATT ACG CCA AGC TCG AAA     52
                           Met Thr Met Ile Thr Pro Ser Ser Lys
                            1               5

TTA ACC CTC ACT AAA GGG AAC AAA AGC TGG TAC CGG GGC CCC CCC TCG    100
Leu Thr Leu Thr Lys Gly Asn Lys Ser Trp Tyr Arg Gly Pro Pro Ser
 10              15                  20                  25

AGG TCG ACG GTA TCG ATA AGC TTG ATA AAC CAT TTA TAC AAT AAG CGT    148
Arg Ser Thr Val Ser Ile Ser Leu Ile Asn His Leu Tyr Asn Lys Arg
             30              35                  40

TGATATAAGT TTGTATATAC GTCATTTCGT TATATCAACA A ATG TTA TCA TAT      201
                                              Met Leu Ser Tyr
                                                          45

TAT ACG TAAAACTGGC TTAAAAAAAA ACGAGGTGTA ACTATA ATG TCT TTT CGC    255
Tyr Thr                                            Met Ser Phe Arg
                                                             50

ACG TTA GAA CTA TTT                                                270
Thr Leu Glu Leu Phe
         55
```

( 2 ) INFORMATION FOR SEQ ID NO:13:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Met Thr Met Ile Thr Pro Ser Ser Lys Leu Thr Leu Thr Lys Gly Asn
 1               5                  10                  15

Lys Ser Trp Tyr Arg Gly Pro Pro Ser Arg Ser Thr Val Ser Ile Ser
            20                  25                  30

Leu Ile Asn His Leu Tyr Asn Lys Arg Met Leu Ser Tyr Tyr Thr Met
            35                  40                  45

Ser Phe Arg Thr Leu Glu Leu Phe
        50                  55
```

RECOMBINANT CVIJI RESTRICTION ENDONUCLEASE

FIELD OF THE INVENTION

The present invention relates generally to isolated purified polynucleotides which encode restriction enzymes and to methods of expressing the restriction enzymes from such polynucleotides. More particularly this invention relates to isolated purified polynucleotides which encode CviJI and related methods for the production of this enzyme.

BACKGROUND OF THE INVENTION

Restriction endonucleases are a group of enzymes originally found to be expressed in a wide variety of prokaryotic organisms. More recently they have also been found to be encoded in vital genomes. These enzymes catalyze the selective cleavage of DNA at generally short sequences, often unique to the individual enzyme. This ability to cleave makes restriction endonucleases indispensible tools in recombinant DNA technology. The increased commercial availability of the isolated enzymes has contributed in large part to the enormous expansion in the field of recombinant DNA technology over the last few years.

In bacteria, the restriction endonuclease provides a mechanism of defense against foreign DNA molecules (e.g., bacteriophage DNA) by virtue of its ability to distinguish and cleave only exogenous DNA, leaving endogenous bacterial DNA unaffected. Viral endonucleases possess the same discerning capabilities, but rather than providing a means for defense, this activity has presumably evolved to cripple the host's ability to replicate its own DNA and allows the virus to assume control of the host's replication machinery.

Bacteria and viruses which express restriction endonucleases necessarily possess the inherent ability to protect their own genome from cleavage by their endogenous endonuclease. The primary mechanism by which this is accomplished is by modifying the organisms own DNA by, for example methylating a base in the recognition sequence which prevents binding and cleavage by the endonuclease. Therefore, to insure viability, the genome of an organism which expresses a restriction endonuclease is almost always heavily modified, usually by methylation of cytosine or adenosine bases. The methylase enzyme which modifies the genome (itself a useful tool in molecular biology) acts in tandem with the endonuclease, either as part of an enzyme complex (restriction/modification complex) or as two distinct entities. Therefore, recognizing that an organism expresses an enzyme with endonuclease activity strongly suggests the expression of an associated modifying methylase enzyme (and vice versa) and this association has led to isolation and cloning of a number of commercially available restriction/modification enzymes for use in the laboratory as discussed below.

Endonucleases act by recognizing nucleotide sequences in a double stranded DNA molecule, binding to the sequence and cutting or cleaving the original DNA molecule into fragments. These fragments can then be isolated and propagated in a variety of ways to produce multiple copies of the desired sequence.

Although restriction endonucleases typically recognize and cut at a specific or defined sequence, in a number of cases the sequence specificity of isolated restriction endonucleases can be altered under appropriate reaction conditions (for example, by modifying glycerol concentration, ionic strength, pH, divalent cation concentration, or other conditions either individually or in combination). This altered specificity has been termed star (*) activity. As will be discussed below, the star activity of a given endonuclease can in some cases be exploited to great advantage in a number of molecular biological techniques.

One of the limitations in the use of restriction endonucleases exists when cleavage of a given sequence is required and no known endonuclease exists which is specific for that particular sequence. Therefore, the continued identification and isolation of unique restriction endonucleases and altered reaction conditions will allow for even more sophisticated manipulation of DNA in vitro.

A number of publications and patents describe the cloning of DNAs encoding restriction endonucleases. Included among theses publications is Kiss. A., et al., *Nucleic Acid Research* 13:6403–6421 (1985), which describes the cloned nucleotide sequence of the BsuRI restriction-modification system isolated from *Bacillus subtillis*. This system is specific for the sequence 5'-GGCC-3' and is defined by two gene products which are transcribed by different promoters. The methylase component of the system shows homology to the methylase from the BspRI and SPR restriction-modification systems.

Nwanko, D. O. and Wilson, G. G. *Gene* 64:1–8 (1988), describe the cloning and expression of the MspI restriction and modification genes isolated from Moraxella sp. This system recognizes the sequence 5'-CCGG-3' and both enzymes are functional in *E. coli*. Evidence indicates that these genes are transcribed in opposite directions, thus are probably under the control of different promoters.

Ashok, K. D., et al., *Nucleic Acids Research* 20:1579–1585 (1992), describe the purification and characterization of cloned MspI methyltransferase, over-expressed in *E. coli*. At low concentrations the enzyme exists as a monomer, but at higher concentrations it exists mainly as a dimer. Polyclonal antibodies to the enzyme cross-react with methyltransferase genes of other modification systems.

Brooks, J. E., et al. *Nucleic Acids Research* 19:841–850 (1991), characterizes the cloned BamHI restriction modification system from *Bacillus subtilis*. The two genes are divergently oriented and separated by an open reading frame which may serve as a transcriptional regulator in the native bacteria.

Slatko, B. E., et al. *Nucleic Acids Research* 15:9781–9796 (1987), describe the cloning, sequencing and expression of the TaqI restriction-modification system. These genes have the same transcriptional orientation, with the methylase gene 5' to the endonuclease gene. *E. coli* clones which carry only the endonuclease gene are viable even in the absence of the methylase gene. This is an unusual case possibly explained by the 65° C. optimal temperature for TaqI restriction and the 37° C. optimal temperature for *E. coli* growth.

Howard, K. A., et al., *Nucleic Acids Research* 14:7939–7951 (1986), describe the cloning of the DdeI restriction modification system from *Desulfovibrio desulfuricans* by a two step method wherein the methylase gene is first cloned and transformed into *E. coli*, followed by the cloning of the endonuclease gene and transformation of this second gene into the methylase-expressing bacteria. In order to maintain cell viability, high levels of methylase expression are required before the endonuclease gene can be introduced into the bacteria.

Ito, H., et al., *Nucleic Acids Research* 18:3903–3911 (1990), describe the cloning, nucleotide sequence and expression of the HincII restriction-modification system. The DNA was isolated from *H. infuenzae* Rc, with the two genes positioned in the same transcriptional orientation.

Shields, S. L., et al., *Virology* 76:16–24 (1990), describe the cloning and sequencing of the cytosine methyltransferase gene M.CviJI from the Chlorella virus IL-3A. The methylase recognizes the sequence (G/A)GC(T/C/G) and shows amino acid sequence homology with 5-methylcytosine methylases isolated from bacteria. DNA encoding the methylase was obtained from the viral genome which was propagated in the green alga host Chlorella.

Xia, Y., et al., *Nucleic Acids Research* 15:6075–6090 (1987), discovered that IL-3A virus infection of Chlorella-like green alga induces the expression of the DNA restriction endonuclease CviJI which has novel sequence specificity. This endonuclease recognizes the sequence PuGCPy (wherein Pu=purine and Py=pyrimidine) but does not cut the sequence PuG$^m$CPy, where $^m$C is 5-methylcytosine.

U.S. Pat. No. 5,137,823, issued Aug. 11, 1992, to Brooks, J. E., describes a two step method for cloning the BamHI restriction modification system wherein the methylase is cloned first and then introduced into a bacterial host. The endonuclease is then cloned and introduced into the methylase expressing bacteria. This two step procedure provides the host DNA protection from cleavage of the subsequently introduced endonuclease.

U.S. Pat. No. 5,200,333, ('333) issued Apr. 6, 1993, to Wilson, G. G., describes a method for cloning restriction and modification genes. Specifically this reference describes the cloning of the TaqI and HaeII systems from *Thermus aquaticus* and *Haemophilus aegypticus*, respectively. In this method, bacterial DNA was initially purified and digested, and the fragments were then cloned into a vector to produce a bacterial DNA library. The library was then transformed into *E. coli* and the cells were plated. Colonies were then scraped from the plate to form a primary cell library. Plasmid DNA from this cell library was purified and digested with the endonuclease of the two gene system. Bacteria which expressed the methylase gene had modified plasmid DNA which was protected from endonuclease activity, while plasmids from bacteria which lacked the intact methylase gene were digested. The resulting, undigested plasmid DNA was then transformed into another bacterial strain and the bacteria were plated. Surviving colonies were again harvested to give a secondary cell library and the entire procedure repeated. Plasmids which code for the complete restriction-modification system presumably survived each round of purification and were enriched. Bacteria which survive several rounds of enrichment were subsequently assayed for both methylase and endonuclease activity.

U.S. Pat. No. 5,196,331, ('331) issued Mar. 23, 1993, to Wilson, G. G. and Nwanko, D., describes a method for cloning the MspI restriction and modification genes. This patent describes a method identical to that of U.S. Pat. No. 5,200,333 ('333). '331 is a continuation-in-part of, and '333 is a continuation of U.S. Ser. No. 707,079 (now abandoned).

As mentioned above, Chlorella virus IL-3A encodes a unique restriction endonuclease called CviJI (Xia et al. *Nucleic Acids Res.* 15:6075–6090 (1987)). IL-3A is a large, polyhedral, plaque-forming phycodnavirus (Francki, R. I. B., et al. *Arch. Virol.* suppl. 2. Springer-Verlag, Vienna (1991)) that replicates in unicellular, eukaryotic green algae, Chlorella strain NC64A (Schuster, A. M., et al. *Virology* 150:170–177 (1986)). The double-stranded DNA genome of IL-3A is approximately 330 kbp (Rohozinski et al., *Virology* 168:363–369 (1989)) and contains 9.7% methylated cytidine (Van Etten, J. L. et al., *Nucleic Acids Res.* 13:3471–3478 (1985)). The cognate methyltransferase of CviJI, M.CviJI, methylates (A/G)GC(T/C/G) sequences and, has been cloned and sequenced (Shields, S. L. et al., *Virology* 176:16–24 (1990)).

CviJI is an unusual restriction endonuclease which is capable of digesting DNA at a two base or three base recognition sequence, depending on the reaction conditions. CviJI normally recognizes the sequence PuGCPy and cleaves between the G and C residues to leave blunt ends (Xia et al. *Nucleic Acids Res.* 15:6075–6090 (1987)). Under relaxed or star conditions (in the presence of 1 mM ATP and 20 mM DTT) the specificity of CviJI can be altered to cleave DNA more frequently. This activity is referred to as CviJI*, for star or altered specificity. However, CviJI* activity is not observed under conditions which favor star activity of other restriction endonucleases.

The use of a two/three base recognition endonuclease, such as CviJI, to improve numerous conventional molecular biology applications as well as permitting novel applications has been described in co-pending U.S. patent application Ser. No. 08/036,481, filed on Mar. 24, 1993. The application discloses methods for generating sequence-specific oligonucleotides from DNA without prior knowledge of the nucleic acid sequence of such DNA, and to methods for cloning and labeling DNA after restriction digestion by a two base recognition endonuclease. The application also teaches methods for generating quasi-random fragments of DNA, methods for cloning, labeling, and sequencing DNA, as well as epitope mapping of proteins. The ability to generate numerous oligonucleotides with perfect sequence specificity or quasi-random distributions of DNA fragments such as is possible with CviJI* has important implications for a number of conventional and novel molecular biology procedures.

Infection of Chlorella species NC64A with the IL-3A virus produces sufficient CviJI restriction endonuclease (CviJI) for research purposes. However, production of commercially useful amounts of CviJI is limited with this system due to the slow growth of Chlorella algae, the large number of contaminating nucleases associated with the virus, and the small yield of enzyme obtained after purification. In addition, biochemical and biophysical characterization of the enzyme, such as molecular weight determination, are difficult from the native source. Because of these limitations it would be useful to clone the gene for CviJI in order to provide an adequate large scale source of enzyme for use as a molecular biological reagent.

BRIEF SUMMARY

In one of its aspects, the present invention provides purified and isolated polynucleotides (e.g., DNA sequences and RNA transcripts thereof) encoding a unique restriction endonuclease, CviJI, as well as polypeptides and variants thereof which display activities characteristic of CviJI. Activities of CviJI include the recognition of specific DNA sequences, binding to these sequences and cleaving the bound DNA into fragments. Preferred DNA sequences of the invention include viral genomic sequences as well as wholly or partially chemically synthesized DNA sequences. Replicas (i.e., copies of the isolated DNA sequences made in vivo or in vitro) of DNA sequences of the invention are also contemplated. A preferred DNA sequence is set forth in SEQ ID NO: 2 herein and is contained as an insert in the plasmid pCJH1.4. In another of its aspects, the invention provides purified isolated DNA encoding a CviJI polypeptide by means of degenerate codons.

Also provided are autonomously replicating recombinant constructions such as plasmid DNA vectors incorporating CviJI sequences and especially vectors wherein DNA encoding CviJI or a CviJI variant is operatively linked to an endogenous or exogenous expression control DNA sequence.

According to another aspect of the invention, host cells such as prokaryotic and eukaryotic cells, are stably transformed with DNA sequences of the invention in a manner allowing the desired polypeptides to be expressed therein. Host cells expressing CviJI and CviJI variant products are useful in methods for the large scale production of CviJI and CviJI variants wherein the cells are grown in a suitable culture medium and the desired polypeptide products are isolated from the host cells or from the medium in which the cells are grown. A preferred host cell is *E. coli*. Still another aspect of the invention is a recombinant CviJI polypeptide.

BRIEF DESCRIPTION OF THE DRAWINGS

FIG. 2 is the nucleotide sequence of 5497 bp of cloned IL-3A viral DNA;

FIG. 4 is the DNA sequence of the CviJI gene with its flanking regions. The predicted amino acid sequence is provided below the nucleotide sequences;

FIG. 10A illustrates the size distribution of DNA fragments produced by partial digestion of DNA by CviJI and fractionated by microcolumn chromatography;

FIG. 10B–C illustrates the size distribution of DNA fragments produced by partial digestion of DNA by CviJI and fractionated by agarose gel electrophoresis;

DETAILED DESCRIPTION

Figure 1:
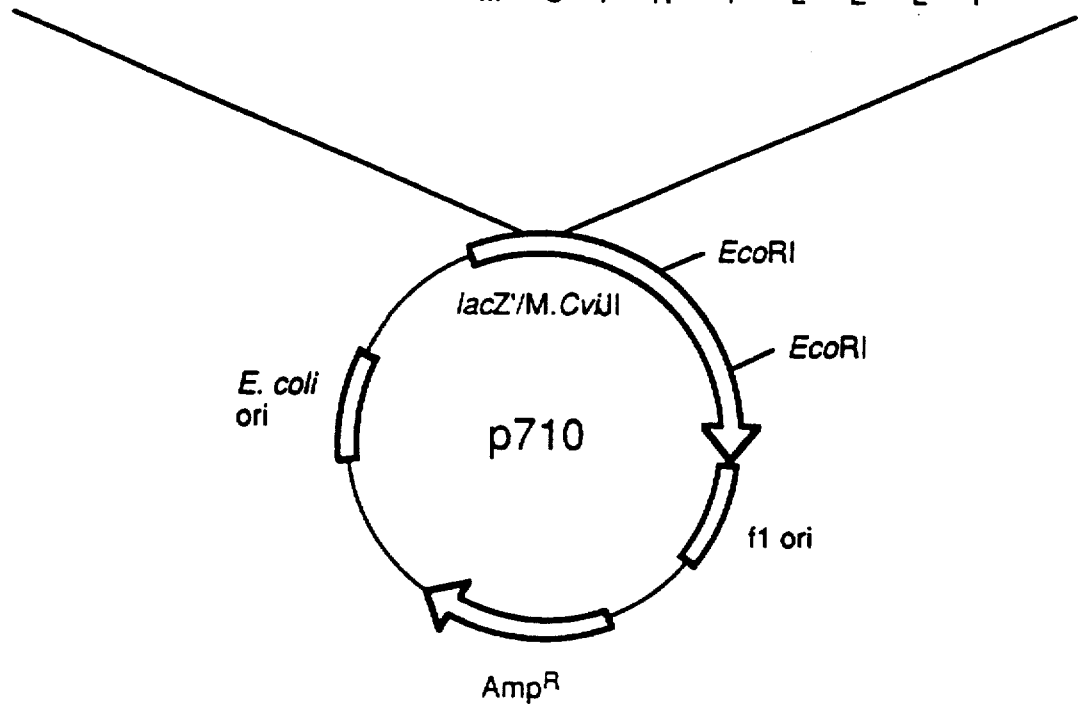
FIG. 1 is a map of the plasmid p710 which contains DNA sequences encoding for the IL-3A viral methyltransferase M.CviJI.

The gene for the restriction endonuclease R.CviJI was cloned into *E. coli* so as to provide an adequate source of R.CviJI for use as a molecular biological reagent. Biologically active CviJI has been purified from *E. coli* to apparent homogeneity. The molecular weight of *E. coli* derived R.CviJI is 32.5 kD by SDS gel electrophoresis. N-terminal amino acid sequence analysis of this protein and comparison to the nucleotide sequence of the gene revealed that the translation of this enzyme is probably initiated with a GTG start codon, instead of the usual ATG initiation codon. The structural gene is 834 nucleotides in length coding for a protein of 278 amino acids (31.6 kD). A second peak of R.CviJI activity which elutes separately from the 32.5 kD form can be seen in the initial stages of enzyme purification. Trace amounts of a larger molecular weight form have not been observed to date. However, the R.CviJI gene does possess an in-frame upstream ATG codon which if translated would yield a predicted 41.4 kD protein. The structural gene for this potentially larger product is 1074 nucleotides in length coding for a putative protein of 358 amino acids.

The present invention is illustrated by the following examples relating to the isolation of a full length viral DNA clone encoding R.CviJI, to the expression of R.CviJI DNA in *E. coli* strain DH5αF'MCR and to purification of R.CviJI from this bacterial stain. More particularly, Example 1 provides for the propagation of IL-3A virus and isolation of vital genomic DNA. Example 2 addresses the improved expression of a clone for the viral methylase M.CviJI. Example 3 describes the strategy for isolating and cloning the viral R.CviJI gene by a forced co-cloning strategy of the M.CviJI gene. Example 4 describes the sequencing of cloned IL-3A genomic DNA and identification of the R.CviJI gene. Example 5 relates the methods for purification of CviJI to homogeneity from an *E. coli* strain, DH5αF'MCR, transformed with a plasmid which encodes the R.CviJI enzyme. Example 6 details the amino acid sequence analysis of the purified R.CviJI enzyme. Example 7 describes the analysis of CviJI* recognition sequences. Example 8 relates to a technique for producing restriction generated oligonucleotides using CviJI. Example 9 to relates the generation of anonymous primers using CviJI. Example 10 describes end-labeling of CviJI restriction generated oligonucleotides. Example 11 describes primer extension labeling of DNA using restriction generated oligonucleotides. Example 12 relates to the use of CviJI in thermal cycle labeling of DNA. Example 13 provides a method for generation of quasi-random DNA fragments using CviJI. Example 14 describes fractionation of CviJI digested DNA by size using spin column chromatography. Example 15 details the relative cloning efficiency of CviJI digested, size-fractionated DNA by gel elution and chromatographic methods. Example 16 describes the comparison of cloning efficiency using lambda DNA fragmented by both sonication and CviJI techniques. Example 17 details the use of CviJI fragmentation for shot gun cloning and sequencing. Example 18 describes the shot gun cloning of lambda DNA using CviJI. Example 19 describes the use of CviJI in epitope mapping techniques.

Example 1

Propagation of IL-3A Virus

The exsymbiotic Chlorella-like alga, NC64A, originally isolated from *Paramecium bursaria* (Karakashian, S. J. and Karakashian, M. W., *Evolution and Symbiosis in the Genus Chlorella and Related Algae*. Evolution 19:368–377 (1965)), was grown and maintained in Bold's basal medium (BBM), (Nichols, H. W. and Bold, H. C. J. Phycol. 1:34–38 (1965)) modified by the addition of 0.5% sucrose, 0.1% protease peptone, and 20 μg/ml tetracycline (MBBM). Cultures were innoculated with $1 \times 10^6$ algae cells/ml and grown at 25° C. in 250 ml of MBBM in 500 ml Erlenmeyer flasks on a rotary shaker (150 rpm) in continuous light (ca. 30 µEi, $m^{-2}$, $sec^{-1}$). Growth was monitored by light scattering measured as $A_{640\ nm}$ and/or by direct cell counts with a hemocytometer.

When the cultures reached approximately $1\times10^7$ algae cells/ml they were innoculated with filter sterilized (0.4 µm nitrocellulose filter, Nucleopore, Pleasanton, Calif.) IL-3A virus at a multiplicity of infection of 0.01 and incubated for an additional 48–72 hours at 25° C. The crude lysate was then centrifuged at 3000 rpm (2000×g) for 10 minutes to remove cellular debris. Nonidet P-40 was then added to 1% (v/v) and the virus was pelleted from the supernatant by centrifuging at 15,000 rpm at 4° C. for 75 minutes in a Beckman No. 30 rotor. The viral pellet was gently resuspended in 0.05M Tris-HCl pH 7.8, and the sample was layered on linear 10–40% sucrose gradients equilibrated with 0.05M Tris-HCl, pH 7.8, and centrifuged for 20 minutes at 20,000 rpm at 4° C. in a Beckman SW28 rotor. The viral band, which was present in the center of the gradient as an opaque band, was removed, diluted with 0.05M Tris-HCl, pH 7.8, and pelleted by centrifugation at 15,000 rpm at 4° C. for 120 minutes in a Beckman No. 80 rotor. The virus was resuspended in a small volume (10 ml) of 0.05M Tris-HCl, pH 7.8, and stored at 4° C.

IL-3A viral DNA was purified from the viral particles using a modification of the protocol described by (Miller, S. A., Dykes, D. D., and Polesky, H. I., *Nucleic Acids Res.* 16:1215 (1988)). Briefly, 100 µl of IL-3A virus ($9.8\times10^{11}$ plaque forming units/ml) was diluted with 400 µl of water and then mixed with 10 µl TEN (0.5M Tris-HCl, pH 9.0, 20 mM EDTA, 10 mM NaCl) and 10 µl of 10% SDS. After incubating at 70° C. for 30 minutes the solution was extracted twice with phenol-chloroform-isoamyl alcohol, extracted once with chloroform, and precipitated with ice-cold ethanol using methods well known in the art and resuspended in 500 µl of $H_2O$. (Ausubel, F. M., Brent, R., Kingston, R. E., Moore, D. D., Seidman, J. G., Smith, J. A. and Struhl, K. (Eds.) (1987) *Current Protocols in Molecular Biology*, Wiley, New York; Sambrook, J., Fritsch, E. F. and Maniatis, T. (1989), *Molecular Cloning: A Laboratory Manual*, Cold Spring Harbor Laboratory Press, Cold Spring Harbor, N.Y.).

Example 2

CviJI Methyltransferase Clone

The CviJI methyltransferase gene (M.CviJI) from Chlorella virus IL-3A was cloned and sequenced by Shields et al., *Virology* 176:16–24 (1990). Briefly, Sau3A partial digest of Chlorella virus IL-3A was ligated to BamHI digested pUC19 and transformed into *E. coli* strain RR1. This library of plasmids was restricted with HindIII (AAGCTT) and SstI (GAGCTC), both of which are inhibited by 5-methylcytidine (5mC) in the AGCT portion of their recognition sequences, and transformed again into RR1 cells. M.CviJI methylates the internal cytidine in (G/A)GC(T/C/G) sequences. If the M.CviJI gene is cloned and expressed appropriately, the plasmid DNA would be expected to be resistant to HindIII and SstI restriction.

The CviJI methyltransferase gene was originally cloned as a 7.2 kb insert, termed pIL-3A.22. Plasmid pIL-3A.22 was only partially resistant to CviJI digestion. Partial digestion is most likely due to the inefficient expression of the M.CviJI gene and the numerous CviJI sites in both the vector (pUC19 has 45 CviJI sites) and in the insert DNA.

The M.CviJI gene was eventually sublocalized to a region of 3.7 kb by subcloning using methods well known in the art (Ausubel, F. M., Brent, R., Kingston, R. E., Moore, D. D., Seidman, J. G., Smith, J. A. and Struhl, K. (Eds.) (1987) *Current Protocols in Molecular Biology*, Wiley, New York; Sambrook, J., Fritsch, E. F. and Maniatis, T. (1989), *Molecular Cloning: A Laboratory Manual*, Cold Spring Harbor Laboratory Press, Cold Spring Harbor, N.Y.) and testing the subcloned DNA for sensitivity/resistance to HindIII, SstI, and CviJI. (Shields et al., supra) The entire sequence was determined and three open reading frames which could code for polypeptides 161, 367, and 162 amino acids, respectively, were identified. The 367 amino acid open reading frame (ORF) was identified as the M.CviJI gene by three criteria: (i) it is the only ORF located in the region identified by transposon mutagenesis; (ii) it has amino acid motifs similar to those of other cytosine methyltransferases; and (iii) a 1.6 kb DraI fragment containing the 367 amino acid ORF (1101 bp) produces the methyltransferase. This 1.6 kb M.CviJI encoding fragment was subcloned into the EcoRV site of pBluescript KS(−) (Stratagene, LaJolla, Calif.), in the same translational orientation as the lacZ' gene of this vector. A physical map of the resulting plasmid termed p710 is shown in FIG. 1.

The plasmid p710 was digested with several endonucleases to indirectly test the efficiency of M.CviJI expression. Fully active methylase should render the plasmid DNA completely resistant to digestion by the following enzymes: HaeIII (which recognizes the sequence GGCC), SacI (which recognizes the sequence GAGCTC), and HindIII (which recognizes the sequence AAGCTT). The plasmid was partially resistant to HaeIII (90%) and SacI (90%), and even less resistant to HindIII (25%) digestion. This lack of complete protection of the plasmid DNA made it impractical to attempt cloning the three/two base restriction endonuclease encoded by the R.CviJI gene. Thus, improvements in the efficiency of M.CviJI expression were required before attempting to clone the R.CviJI gene.

The translation efficiency of the M.CviJI gene was improved by removing extraneous 5' open reading frames, creating a perfect fusion of the lacZ' Shine-Delgarno sequence with the methyltransferase start codon (see FIG. 1). This was achieved by site-specific oligonucleotide mutagenesis, using the oligomer 5'-CAATTTCACACAGGAAACAGCTAT-GTCTTTTCGCACGTTAGAAC-3' (SEQ ID NO: 1) to precisely remove the intervening lacZ' DNA. The relevant DNA sequences are indicated in FIG. 1 (SEQ ID NO: 12). The mutagenesis was facilitated by converting the double stranded plasmid DNA of p710 to single-stranded DNA by co-infecting the *E. coli* host strain with the helper phage R408 (Russel, M., Kidd, S. and Kelly, M. R. *Gene* 45:333–338), using methods well known in the art. The mutagenesis reaction was completed using a commercially available kit according to the manufacturer's instruction (Mutagene, Bio-Rad, Hercules, Calif.). The oligonucleotide was annealed to the single-stranded plasmid, extended in the presence of T4 DNA polymerase, ligated using T4 DNA ligase, and transformed into competent SURE™ cells (Stratagene, La Jolla, Calif.). Transformed cells were then grown overnight as a pool, the DNA isolated and purified.

Enrichment for the mutagenized plasmids was made possible by virtue of the loss of an XhoI site located in the sequence that was deleted by mutagenesis. Enrichment was accomplished by digesting the isolated, purified plasmid DNA with XhoI, followed by dephosphorylation with calf intestinal alkaline phosphatase (CIAP), and transformed into SURE cells. Plasmid DNA was isolated from 18 individual colonies and the DNA tested for resistance to XhoI. Plasmid DNA from 11 colonies were resistant to XhoI digestion, indicating that they lacked the deleted sequence. Five of these plasmids were restricted with HaeIII, HindIII, PvuII (which recognizes the sequence CAGCTG), and CviJI. All five appeared 100% resistant to these enzymes. Four of the plasmids were sequenced and the deletion was confirmed as being correct. One of these, pBMC5, was chosen for further modification.

Example 3

Forced Co-Cloning of R.CviJI

The location of the R.CviJI gene on the IL-3A virus genome was inferred as being 3' to the M.CviJI gene for two reasons: 1) the cloned DNA sequence 5' to the M.CviJI gene did not produce a restriction activity; and 2) several attempts to clone the DNA 3' to the M.CviJI gene resulted in deletions/rearrangements of this downstream region. This information permitted a forced co-cloning strategy to obtain the restriction endonuclease gene. This strategy uses a deletion derivative of pBMC5 lacking the 3' half of the M.CviJI gene. Digestion of the IL-3A genome with the same enzyme used to create the M.CviJI deletion, followed by ligation of the respective DNAs, transformation, and digestion with enzymes incapable of recognizing methylated DNA (e.g., HaeIII, HindIII, PvuII, CviJI, etc.) should force the selection of clones which have a restored M.CviJI gene (and thus active methylase enzyme), as well as downstream DNA. Thus, if a clone is found to be CviJI resistant, the 3' half of M.CviJI must have been restored, and downstream DNA containing the R.CviJI gene, at least in part, would presumably be cloned.

The details of this cloning strategy are as follows. pBMC5 has two EcoRI sites, one approximately in the middle of the M.CviJI gene, while the other site lies in the vector DNA, 3' to the M.CviJI gene (see FIG. 1). pBMC5 was restricted with EcoRI and ligated at a dilute concentration (10–50 ng/μl) to favor circularization without the 3' M.CviJI fragment. The reaction mixture was then transformed into competent SURE cells and plated on TY agar containing ampicillin. Plasmid DNA from the resulting colonies was tested for the lack of this EcoRI fragment by digestion with EcoRI. One of these clones, pBMC5RI, was used for the subsequent co-cloning work. Plasmid pBMC5RI was digested with EcoRI and dephosphorylated using CIAP. IL-3A genomic DNA was then digested to completion with EcoRI. The EcoRI digested pBMC5RI and IL-3A DNAs were combined at a ratio of 1:3 in a ligation reaction using T4 DNA ligase, and the products of the ligation reaction were subsequently used to transform competent SURE cells. The pBMC5RI/IL-3A transformants were not plated, but rather grown overnight in culture as a library or pool of cells. The cells were harvested the next day and DNA was isolated and purified. Isolated, purified DNA was digested with HaeIII, dephosphorylated with CIAP, and transformed into competent SURE cells. The cells were then plated and grown overnight. Six colonies grew, of which only one containing the plasmid, pCJH1.4, was resistant to HaeIII. The plasmid pCJH1.4 was found to encode CviJI restriction activity. Plasmid pCJH1.4 was further characterized to localize the gene for CviJI by deletion analysis, subcloning experiments, and sequencing. The plasmid pCJH1.4 was deposited with the American Type Culture Collection on Jun. 30, 1993 under Accession Number 69341.

Example 4

Sequencing of Cloned IL-3A DNA Containing CviJI Gene

The EcoRI fragment cloned into pCJH1.4 (as described in Example 3) is 4901 bp in length. Except for the 519 bp corresponding to the 3' portion of the M.CviJI gene, the remainder of the 4901 bp EcoR I fragment cloned into pCJH1.4 was sequenced using the SEQUAL DNA Sequencing System (CHIMERx, Madison, Wis.) by methods well known in the art. Sequencing was accomplished using three approaches: 1) primer walking on pCHJ1.4, 2) cloning various restriction endonuclease digests of pCHJ1.4 into an M13 type sequencing vector; and 3) sequencing various restriction endonuclease deletion derivatives of pCHJ1.4. The nucleotide sequence of 5497 bp of IL-3A vital DNA is shown in FIG. 2 and set forth in SEQ ID NO.: 2.

Figure 3:
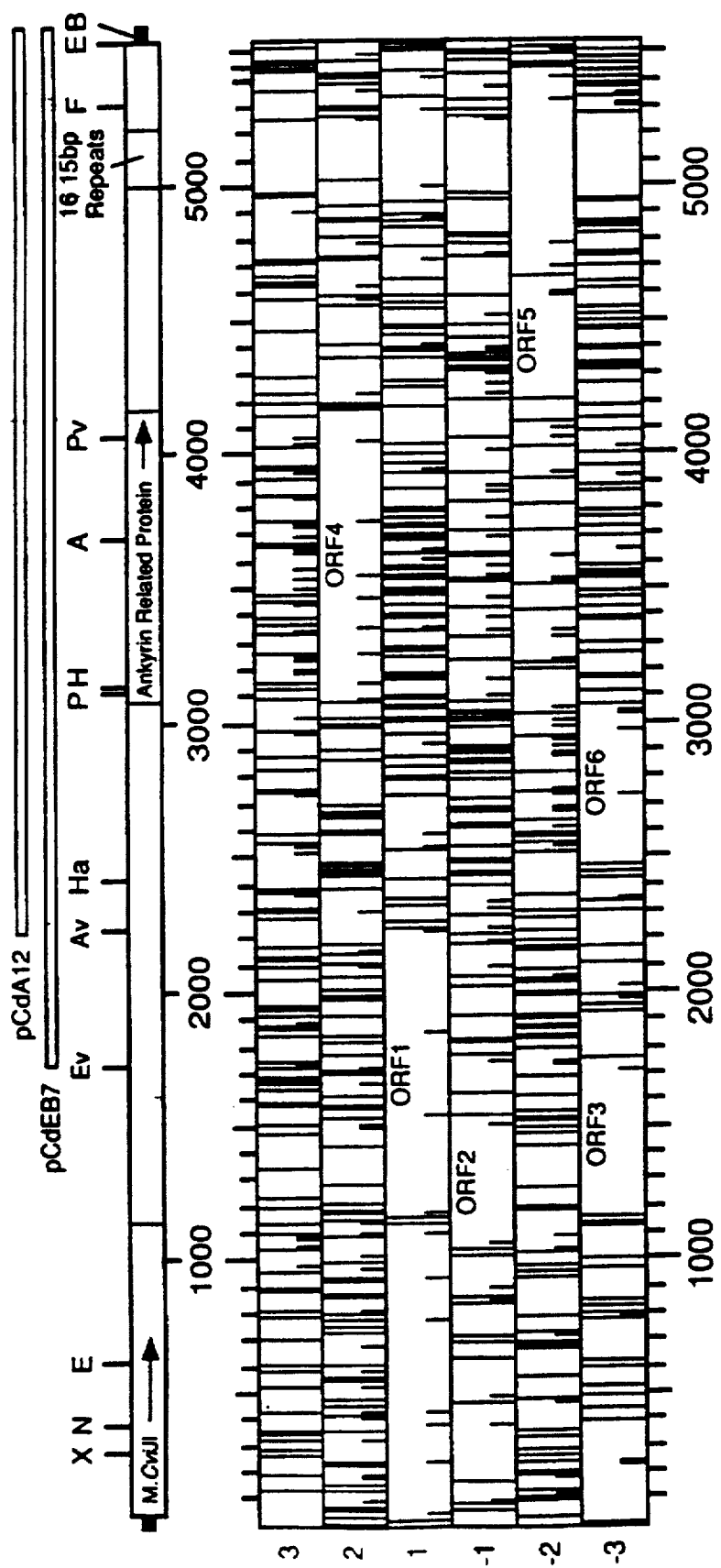
FIG. 3 is a restriction map of the cloned IL-3A viral DNA, including the identified open reading frames.

Six open reading frames (ORF) of 1155 bp (ORF1), 468 bp (ORF2), 555 bp (ORF3), 1086 bp (ORF4), 397 bp (ORF5) and 580 bp (ORF6) which could code for polypeptides containing 358 (41.4 kD), 156 (19.4 kD), 185 (20.3 kD), 362 (38.9 kD), 132 (14.5 kD) and 193 (21.9 kD) amino acids, respectively, were identified (see FIG. 3). ORFs 4–6 do not code for the R.CviJI gene, as the deletion derivative pCdA12, which lacks the DNA between the AvaI and BamHI sites (see FIG. 3), does produce CviJI restriction endonuclease activity. In addition, the deletion derivative pCdEB7, lacking the DNA between the EcoRI and BamHI sites, did not produce CviJI activity. Thus ORF1 or ORF3 were the most likely candidates for encoding the R.CviJI gene. The sequence of the 1155 bp ORF1 (SEQ ID NO: 3), its deduced amino acid sequence (SEQ ID NO: 4) (as shown in capital letters), plus flanking bases, is presented in FIG. 4. The vertical line in FIG. 4 and the associated arrow indicate where the DNA sequence from pJCH1.4 diverges from that of pIL-3A.22-8 (Shields, S. L., et al., Virology 76:16–24, 1990). This open reading (ORF1) frame is believed to represent the CviJI gene because 14 out of 15 N-terminal amino acids from the protein sequence (see Example 6) matched the predicted translation product of the nucleic acid sequence (FIG. 4). Also, the 32.5 kD molecular weight of the homogeneously purified enzyme described in Example 5 matched the predicted translation product of the nucleic acid sequence (31.6 kD) if the encoded protein was translated beginning at the GTG codon located at nucleotides 299–301 (FIG. 4), instead of the 5' ATG codon located at nucleotides 59–61. This possibility is not surprising in light of the fact that approximately 10% of prokaryotic and eukaryotic gene products begin translation with a GTG start codon, rather than the usual ATG codon (Kozak, M., Microbiol. Rev. 47:1–45 (1983); Kozak, M. J. Cell. Biol. 108:229 (1989); Gold, L. et al., Annu. Rev. Microbiol. 35:365–403 (1981)). The structural gene was identified to be 834 nucleotides in length, coding for a protein of 278 amino acids (31.6 kD) and is set forth in SEQ ID NO: 4. It is also interesting to note that the CviJI gene was shown to possess an in-frame, upstream ATG codon which if translated could yield a protein with a predicted molecular weight of 41.4 kD (FIG. 4). A larger molecular weight form possessing CviJI restriction activity has not been detected by SDS gel electrophoresis. However, a second peak of CviJI activity which eluted separately from the 32.5 kD form was detected in the initial stages of enzyme purification. The DNA sequence which could theoretically code for a larger form of CviJI would be approximately 1074 nucleotides in length (assuming it starts at the upstream ATG codon) and would code for a protein of 358 amino acids.

Example 5

Purification of Recombinant CviJI Restriction Endonuclease

Initially, 20 ml of LB medium (plus 100 μg/ml ampicillin) were inoculated with a 1 ml stock of *E. coli* transformed with the plasmid pCJH1.4 described above and grown overnight at 37° C. with shaking. The next day, 20 ml of this initial overnight culture was used to inoculate another 1 liter of LB medium and grown overnight. The following day, 50 liters of TB medium (12 g Bacto-Tryptone, 24 g Bacto Yeast Extract, 4 ml glycerol, 2.31 g $KH_2PO_4$, 12.54 g $K_2HPO_4$, 0.1 g $MgSO_4$, 100 μg/ml ampicillin, and water to 1 liter) were inoculated with an aliquot of the secondary overnight culture and grown at 37° C. with 20 liters/min aeration at 200 RPM, until the $OD_{595\ nm}$ reached 1.0 unit. Vigorous aeration was essential for CviJI expression and a typical yield contained 70 g of cell paste after centrifugation.

The cell pellet was immediately resuspended in lysis buffer A (30 mM Tris-HCl, pH 7.9 at 4° C., 2 mM EDTA, 10 mM beta-mercaptoethanol, 50 μg/ml phenylmethylsulfonyl fluoride (PMSF), 20 μg/ml benzamidine, 2 μg/ml 0-phenantroline, 0.7 μg/ml pepstatin) at a volume of 3 ml of buffer A per 1 g of cells. The cell suspension was then passed through a Manton-Gaulin cell disrupter (Gaulin Corporation, Everett, MA) twice and centrifuged for 1 hr (8000 RPM, Sorvall GS3 Rotor) at 4° C. To the supernatant, solid NaCl was added to a final concentration of 200 mM, and 10% polyethyleneimine (PEI) solution slowly added to a final concentration of 1%. The mixture was stirred for 3 hr, and then centrifuged 30 min, at 4° C., 8000 RPM (Sorvall GS3 Rotor). Solid ammonium sulfate was then added to the supernatant at 0.5 g/ml and the mixture was stirred overnight at 4° C. The precipitated proteins were centrifuged for 1 hr. (8000 RPM, Sorvall GS3 Rotor) at 4° C. and the resulting pellet dissolved in 100 ml of buffer B (10 mM $K/PO_4$, pH 7.2, 0.5 mM EDTA, 10 mM beta-mercaptoethanol, 50 mM NaCl, 10% glycerol, 0.05% Triton X-100, 50 μg/ml PMFS, 20 μg/ml benzamidine, 2 μg/ml o-phenanthroline, 0.7 μg/ml pepstatin). The dissolved protein solution was then dialysed (14 kD cut-off) for 12 hours against three 1 liter changes of buffer B. The dialyzed solution was then diluted to 600 ml with buffer B and applied to a 5×20 cm phosphocellulose P11 (Whatman) column (flow rate 100 ml/hr).

The column was then washed with 1.5 liter of buffer B followed by a 0–1.5M NaCl gradient in buffer B (5 liters). R.CviJI eluted at approximately 600 mM NaCl. The active fractions were then pooled and concentrated to 50 ml with a 76 mm Amicon YM10 membrane. The resulting solution was then diluted to 300 ml with buffer C (20 mM Tris-acetate, pH 7.4 at 4° C., 2 mM EDTA, 10 mM beta-mercaptoethanol, 50 mM NaCl, 10% glycerol, 0.01% Triton X-100, 50 μg/ml PMFS, 20 μg/ml benzamidine, 2 μg/ml o-phenanthroline, 0.7 μg/ml pepstatin) and applied to 2.5×7 cm Heparin-Sepharose column at a flow rate of 25 ml/hr.

After a 400 ml wash with buffer B, R.CviJI was eluted with a 1.5 liter gradient of 0–1.3M NaCl in buffer C. CviJI eluted at approximately 400 mM NaCl. The most active fractions were pooled and applied to a 2.5×7 cm Blue-agarose column equilibrated in buffer D (20 mM Tris-acetate pH 8.0, 1 mM EDTA, 7 mM beta-mercaptoethanol, 30 mM NaCl, 10% glycerol, 0.01% Triton X-100, 50 μg/ml PMFS, 20 μg/ml benzamidine, 2 μg/ml o-phenanthroline, 0.7 μg/ml pepstatin). After a 500 ml wash with buffer D, CviJI was eluted with a 0–1.5M NaCl gradient (1.5 l) in buffer D.

Active fractions were dialyzed against buffer G (10 mM K/PO4 pH 7.0 (4° C.), 10 mM beta-mercaptoethanol, 50 mM NaCl, 10% glycerol, 0.01% Triton X-100, 50 μg/ml PMFS, 20 μg/ml benzamidine, 2 μg/ml o-phenanthroline, 0.7 μg/ml pepstatin) and loaded (20 ml/h) onto a ceramic HTP column (American International Chemical, Natick, Mass.) (1.5×3 cm), equilibrated in buffer F (20 mM Tris-HCl pH 8.0, 0.5 mM EDTA, 3 mM DTT, 50 mM K-acetate, 5 mM Mg acetate, 50% glycerol). After washing with 100 ml of buffer F, a 400 ml gradient 0–0.9M $K/PO_4$ in buffer F was run. The HTP column was washed with buffer G, containing 3 mg/ml BSA, then with 1M phosphate buffer and reequilibrated in buffer G. The active fractions were then pooled and concentrated using a TM10 membrane to a final volume of 3–4 ml. This concentrate was then applied to a 2.5×95 cm Sephadex G-100 column, equilibrated in buffer E (20 mM Tris-HCl pH 7.5 (4° C.), 5 mM Mg-Acetate, 2 mM EDTA, 10 mM beta-mercaptoethanol, 100 mM NaCl, 5% glycerol, 0.01% Triton X-100, 50 μg/ml PMFS, 20 μg/ml benzamidine, 2 μg/ml o-phenanthroline, 0.7 μg/ml pepstatin) at a flow rate of 6 ml/hr, and 3 ml fractions collected. Active fractions were dialyzed against storage buffer F.

The molecular weight of the purified CviJI was determined by comparison to known protein standards on a denaturing 10% SDS polyacrylamide gel and a single band migrating with an apparent molecular weight of 32.5 kilodaltons was seen indicating that by these criteria, CviJI was purified to homogeneity.

Example 6

N-Terminal Amino Acid Sequence of R.CviJI

To confirm that the restriction endonuclease encoded by the insert in pCJH1.4 was CviJI the sequence of the first 15 N-terminal amino acids of purified CviJI was determined by the Edman degradation method using an Applied Biosystems (Foster City, Calif.) 477A Liquid Phase Protein Sequencer with an on-line 120A PTH Analyzer. The results of that analysis are shown in Table 1.

TABLE 1

| N-Terminal Amino Acid Analysis of CviJI | | | | | | |
|---|---|---|---|---|---|---|
| Amino Acid # | Retention Time (min) | pmol (Raw) | Pmol (−bkgd) | Pmol (+lag) | Pmol Ratio | Amino Acid ID |
| 1 | 9.17 | 6.11 | 3.86 | 5.10 | 34.53 | THR, MET, ARG, OR LYS |
| 2 | 10.32 | 3.92 | 1.54 | 1.82 | 9.96 | GLU |
| 3 | 10.33 | 4.28 | 2.22 | 2.18 | 11.96 | GLU |
| 4 | 27.37 | 2.23 | 1.49 | 1.72 | 7.64 | LYS |
| 5 | 27.35 | 2.37 | 1.66 | 1.67 | 7.39 | LYS |
| 6 | 17.95 | 3.37 | 2.76 | 2.81 | 9.48 | ARG |
| 7 | 28.10 | 3.19 | 1.73 | 2.08 | 6.09 | LEU |
| 8 | 13.58 | 3.58 | 2.11 | 2.49 | 12.08 | ALA |
| 9 | 28.10 | 3.23 | 1.68 | 1.58 | 4.63 | LEU |
| 10 | 18.17 | 0.71 | 0.78 | 0.36 | 1.21 | ILE |
| 11 | 10.30 | 1.65 | 0.78 | 0.96 | 5.26 | GLU |
| 12 | 9.72 | 8.03 | 0.41 | 1.31 | 3.25 | LYS |
| 13 | 8.53 | 1.54 | 0.53 | 0.55 | 2.97 | GLN |
| 14 | 18.18 | 2.19 | 1.74 | 1.67 | 5.63 | ARG |
| 15 | 26.80 | 3.33 | 0.43 | — | 0.89 | ILE |

Abbreviations used: threonine (THR), methionine (MET), arginine (ARG), lysine (LYS), glutamic acid (GLU), leucine (LEU), alanine (ALA), isoleucine (ILE) and glutamine (GLN).

The results of this analysis confirm that the protein encoded by the DNA insert in pCJH1.4 (ORF1) is CviJI.

The following Examples illustrate some of the unique properties of and important uses for CviJI.

Example 7

Analysis of CviJI* Recognition Sequences

The CviJI* recognition sequence (see Xia, et al., *Nuc. Acids Res.* 15: 6025–6090, 1987) was deduced by cloning and sequencing CviJI* digested pUC19 DNA fragments. A complete CviJI* digest of pUC19 was ligated to an M13mp18 cloning derivative for nucleotide sequence analysis. The sequence of the entire insert was read in order to determine which sites were or were not utilized. A total of 100 clones were sequenced, resulting in 200 CviJI* restricted junctions, the data for which are compiled in Table 2.

NGCN sites, it may be referred to as a 2.25-base recognition endonuclease.

In addition to the restricted sites, those sites which were not cleaved by CviJI* conditions were also compiled for analysis, as shown in Table 2. A total of 116 non-cleaved NGCN sites were found in the 100 inserts which were sequenced. PyGCPu sites represented the largest class of non-cleaved sites (52.6%). In only two cases were PuGCPy sites found not to be cleaved. An approximately equal fraction of R1 and R2 sites were not cleaved as were found cleaved (22.4% versus 25.5% for R1 and 23.3% versus 27.0% for R2). Based on the frequency of cleavage, or lack thereof, a hierarchy of restriction under CviJI* conditions is evident, where PuGCPy>>PuGCPu=PyGCPy.

TABLE 2

| Classification Group | NGCN Recognition Sequence | CviJI* Sits Found in pUC19 (%) | CviJI* Sites Cleaved (%) | Sites Not Cleaved (%) | Pu/Py Structure |
|---|---|---|---|---|---|
| Distribution of CviJI* Sites as Assayed by Cloning and Sequencing | | | | | |
| Normal (N) | A C | AGCC 9 (4.4) | 23 (11.5) | 1 (0.9) | PuPuPyPy |
|  | G C | GGCC 11 (5.4) | 24 (12.0) | 1 (0.9) |  |
|  | G T | GGCT 10 (4.9) | 13 (6.5) | 0 (0.0) |  |
|  |  | AGCT (7.3) | 35 (17.5) | 0 (0.0) |  |
|  |  | 45 (22.0) | 95 (47.5) | 2 (1.7) |  |
| Relaxed (R1) | C C | CGCC 11 (5.4) | 11 (5.5) | 4 (3.5) | PyPuPyPy |
|  | G C | TOCC 12 (5.9) | 13 (6.5) | 10 (8.6) |  |
|  | T T | TGCT 10 (4.9) | 10 (5.0) | 5 (4.3) |  |
|  |  | CGCT 22 (10.7) | 17 (8.5) | 7 (6.0) |  |
|  |  | 55 (26.0) | 51 (25.5) | 26 (22.4) |  |
| Relaxed (R2) | A A | AGCA 16 (7.3) | 13 (6.5) | 5 (4.3) | PuPyPuPu |
|  | G C | GGCA 8 (3.9) | 11 (5.5) | 3 (2.6) |  |
|  | G G | AGCG 11 (5.4) | 12 (6.0) | 11 (9.5) |  |
|  |  | GGCG 22 (10.7) | 18 (9.0) | 8 (6.9) |  |
|  |  | 57 (27.8) | 54 (27.0) | 27 (23.3) |  |
| Relaxed (R3) | C A | CGCA 10 (4.9) | 0 | 12 (10.4) | PyPuPyPu |
|  | G C | TGCA 13 (6.3) | 0 | 19 (16.4) |  |
|  | T G | CGCG 10 (4.9) | 0 | 27 (23.3) |  |
|  |  | TGCG 15 (7.3) | 0 | 3 (2.6) |  |
|  |  | 48 (23.4) | 0 | 61 (51.6) |  |
|  |  | Total 205 | 200 | 116 |  |

The dinucleotide GC is found at 205 sites in pUC19. These GC sites (shown in Table 2) can be divided into four classes based on their flanking Pu/Py structure, the normal recognition sequence (N) and three potential classes of relaxed sites (R2 and R3). As seen in Table 2, the fraction of such NGCN sites which belong to each classification is roughly equal (22.0%–27.8%). A total of 200 CviJI* restricted junctions were analyzed by sequencing 100 cloned inserts. If CviJI* cleaved at all NGCN sites without sequence preferences, it would be expected that the fraction of each classification should be restricted approximately equally. Instead, most of the sites cleaved by this treatment were found to be normal, or PuGCPy sites (47.5%). R1 (PyGCPy) and R2 (PuGCPu) restricted sites were found at nearly the same frequency (25.5 % and 27.0%, respectively). Out of 200 CviJI* junctions, no R3 (PyGCPu) restricted sites were found. Thus, CviJI* cleaves all NGCN sites except for PyGCPu. As CviJI* cleaves 12 out of 16 possible

Example 8

CviJI* Restriction Generated Oligonucleotides

Due to the high frequency of CviJI or CviJI* restriction, it is possible to generate useful oligonucleotides by digestion and a heat denaturation step as described above. The size and number of the resulting oligonucleotides are important for subsequent applications such as those described above. If for example, an oligonucleotide is to be used with a large genome, it has to be long enough so that the sequence detected has a probability of occurring only once in the genome. This minimum length has been calculated to be 17 nucleotides for the human genome (Thomas, C. A., Jr. *Prog. Nucl. Acid Res. Mol. Biol.*, 5:315 (1966)). Oligonucleotides used for sequencing or PCR amplification are generally 17–24 bases in length. Oligomers of shorter length will often bind at multiple positions, even with small genomes, and thus will generate spurious extension products. Thus, an enzymatic method for generating oligomers should ideally result in polymers greater than 18 bases in length.

Figure 5A:
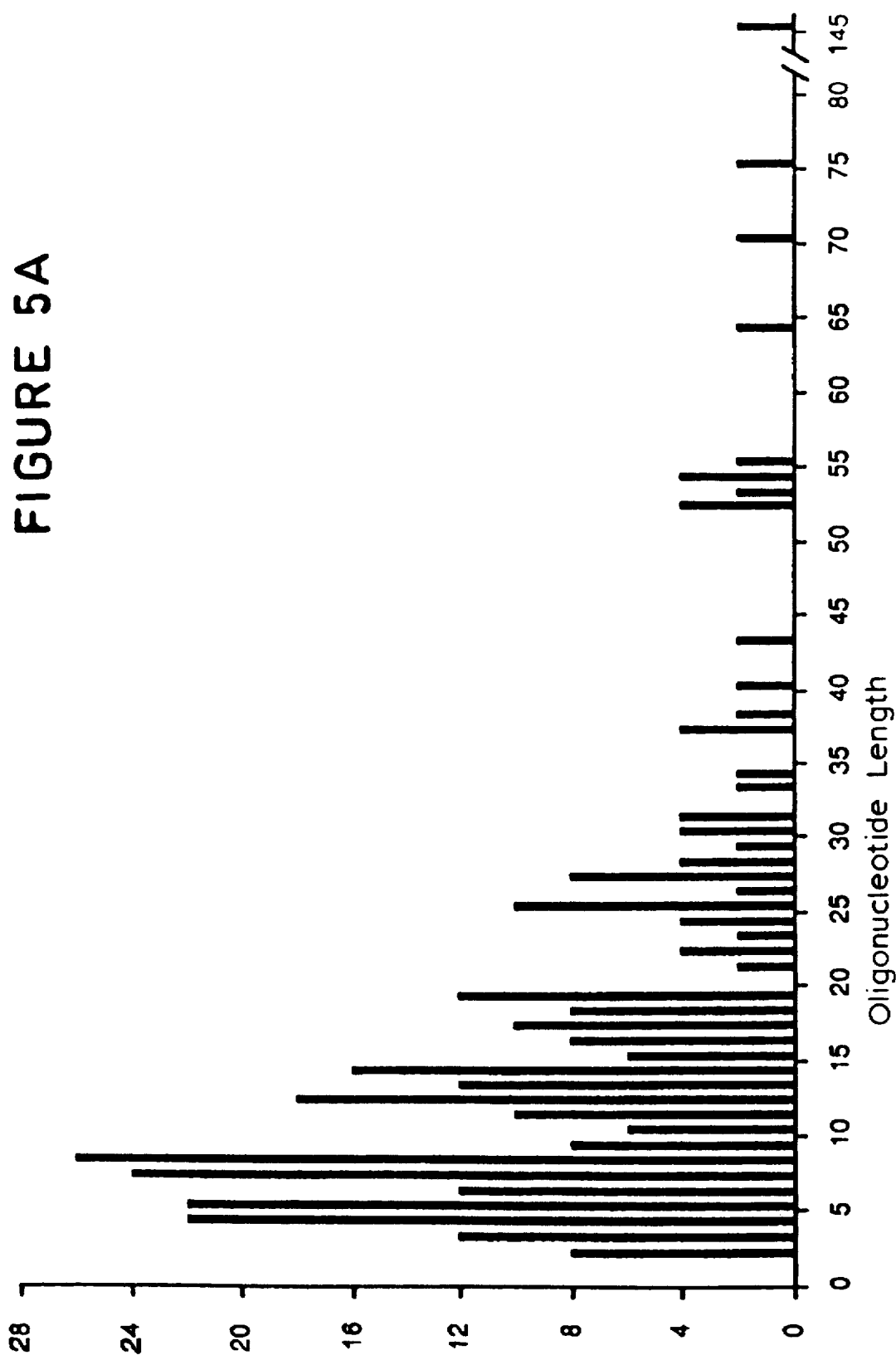
FIG. 5A depicts the theoretical frequency and distribution of CviJI* restriction generated oligomers of individual lengths.
Figure 5B:
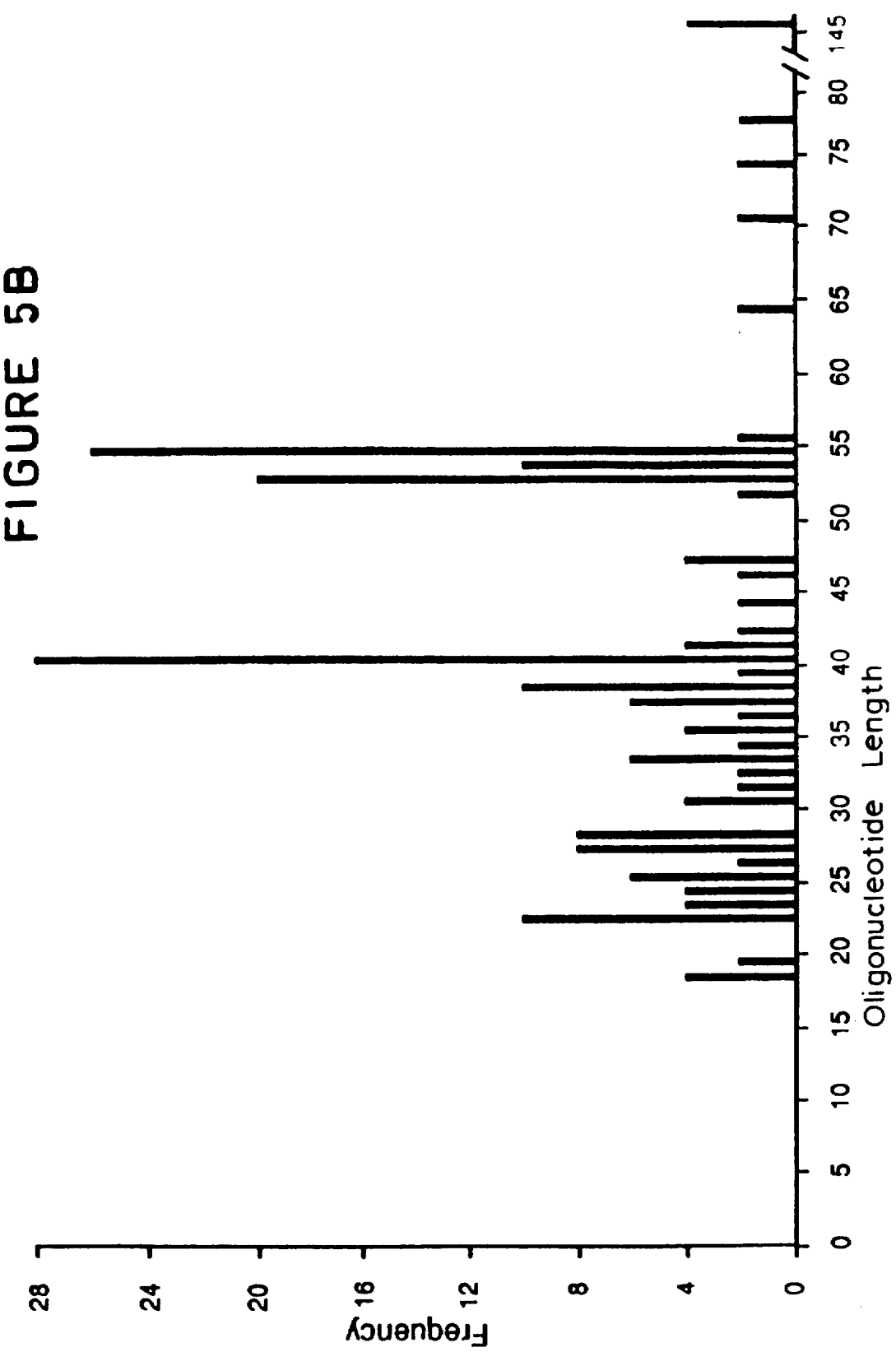
FIG. 5B shows the actual frequency and distribution of CviJI* restriction generated oligomers of various lengths.

The theoretical number of pUC19 CviJI* restriction-generated oligomers is 314 (157 CviJI* restriction fragments×2 oligomers/fragment), the size distribution of which is shown in panel A of FIG. 5. Most of the expected CviJI* restriction-generated oligomers (about 75%) are smaller than 20 bp. This assumes that CviJI is capable of restricting DNA to very small fragments, the shortest of which would be 2 bp. However, in practice, about 93% of the cloned CviJI* fragments were 20–56 bp in size, and 3% of the fragments generated by CviJI* were smaller than 20 bp (panel B of FIG. 5). This suggests that CviJI* is not able to bind or restrict those fragments below a certain threshold length. Since the smallest observed fragment is 18 bp, it may be assumed that this length is the minimal size which can be generated from a given larger fragment. Whatever the reason for this phenomenon, CviJI* treatment of DNA produces a small range of oligomers (mostly 20–60 bases in length), most of which are a perfect size class for molecular biology applications.

Example 9

Anonymous Primer Cloning

Primers are critical tools in many molecular biology applications such as PCR, sequencing, and as probes. Anonymous primers are useful as sequencing primers for genomic sequencing projects, as probes for mapping chromosomes, or to generate oligonucleotides for PCR amplification.

The Anonymous Primer Cloning (APC) method is a variation of shotgun cloning in that unknown sequences of DNA are being randomly cloned. However, unlike CviJI shotgun cloning, wherein a partial CviJI** digest of DNA is cloned, anonymous primer cloning utilizes a complete CviJI* digest to restrict large DNAs into small fragments 20–200 bp in size. These small fragments are cloned into a unique vector designed for excising the anonymous DNA as labeled primers. The strategy for this method is illustrated in FIG. 6.

Figure 6A:
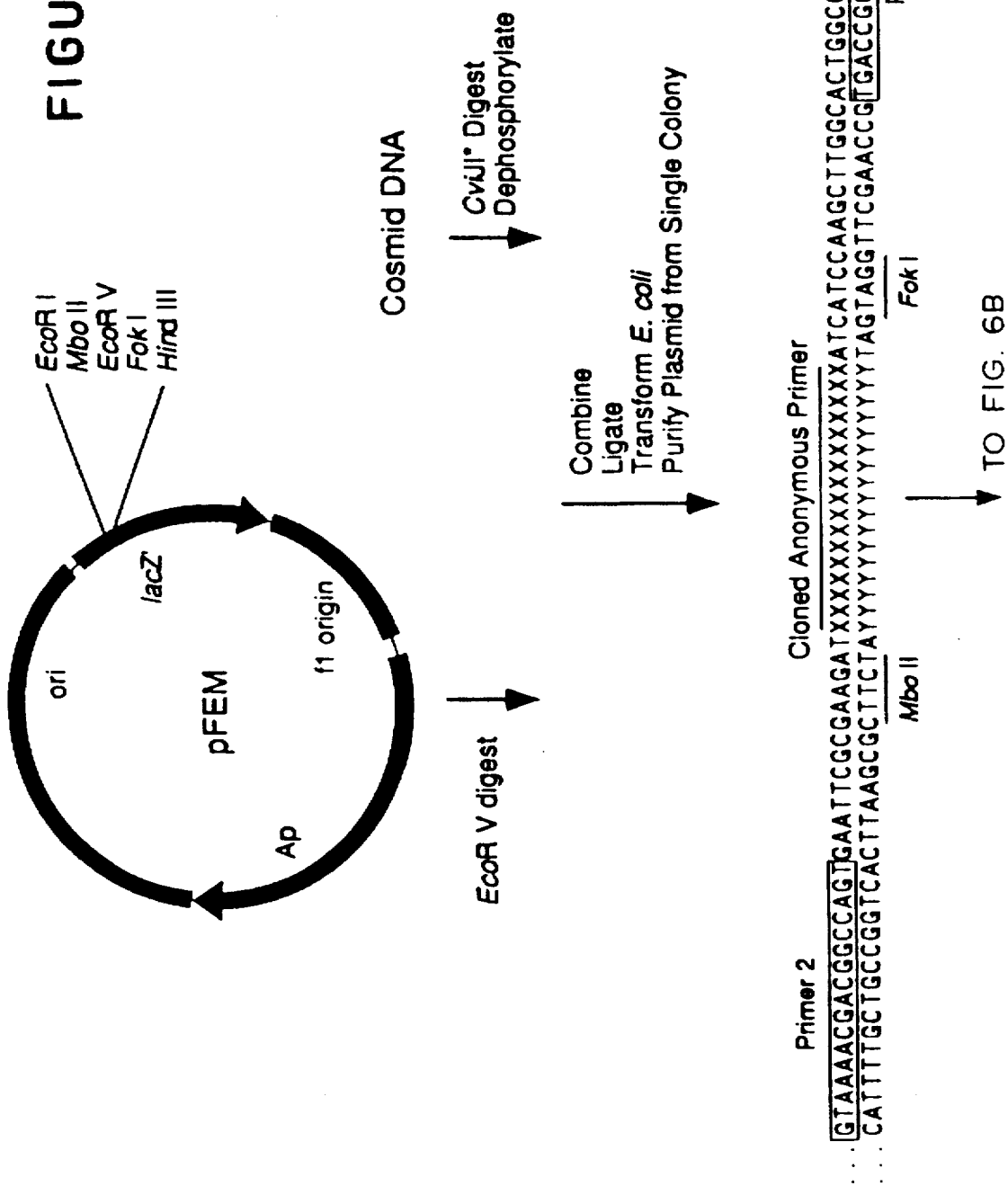
FIG. 6 is a flow chart depicting anonymous primer cloning.
Figure 6B:
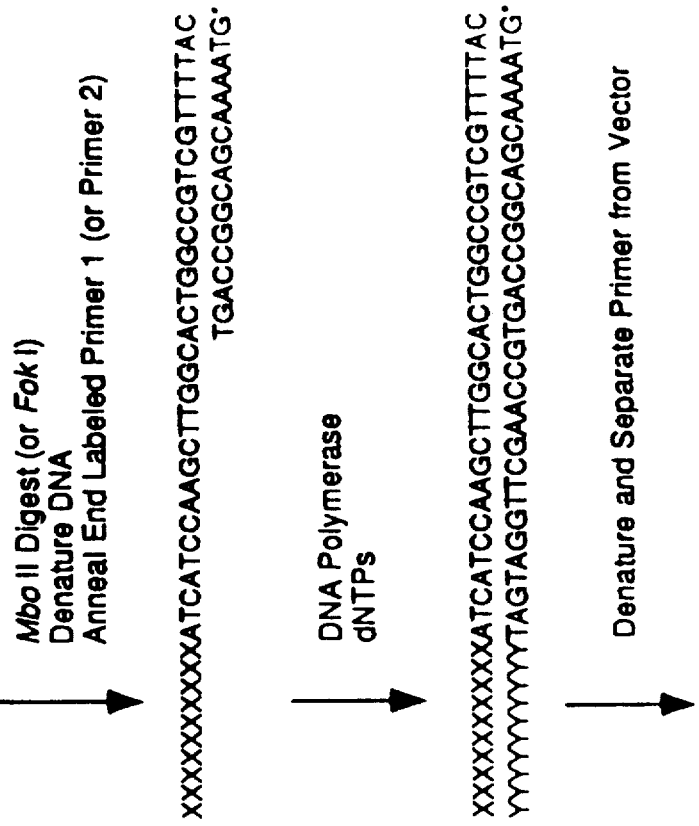

As illustrated in FIG. 6, the APC strategy reduces large DNAs to small fragments, which are cloned and excised for use as primers. Plasmid pFEM has a unique arrangement of the restriction sites for MboII and FokI, which permits DNA cloned into the EcoRV site to be excised without associated vector DNA. This is possible because FokI cleaves 9/13 bases to the left of the recognition site shown in pFEM and MboII cleaves 8/7 bases to the right of the recognition site shown in pFEM, which is well into the cloned anonymous sequence. After MboII or FokI restriction, a known flanking primer is annealed (primer 1 or 2) and extended using a DNA polymerase and dNTPs. The primer is previously end-labeled, or alternatively, one or more of the dNTPs is radioactive.

After denaturation of the newly synthesized DNA and separation from its cognate template, the labeled anonymous primer is ready for use in sequencing the original template from which it was subcloned. The presence of the pFEM vector sequence fused to the anonymous sequence does not influence the enzymatic extension of this primer from its unique binding site, as the vector DNA is at the 5' end and the unique sequence is located at the 3' end (all polymerases extend 5' to 3'). Both the top and bottom strand primers may be excised from pFEM due to the symmetrical placement of restriction sites and flanking primer binding sites. Thus, two primers may be derived from each cloning event. APC is particularly well suited to the genomic sequencing strategy of Church and Gilbert *Proc. Natl. Acad. Sci. USA* 81:1991–1995 (1984), although its utility is not limited thereto.

Example 10

End Labeling of Restriction-Generated Oligonucleotides

As is clear from the foregoing examples, digesting DNA with CviJI* provides the ability to generate sequence-specific oligonucleotides ranging in size from 20–200 bases in length with an average length of 20–60 bases. Sequence specific oligonucleotides generated by CviJI* digestion may be labeled directly at the 5'-end or at the 3'-end using techniques well known in that art.

For example, 5'-end labeling may be accomplished by either a forward reaction or an exchange reaction using the enzyme T4 polynucleotide kinase. In the forward reaction, $^{32}P$ from $[\gamma^{32}P]ATP$ is added to a 5' end of an oligonucleotide which has been dephosphorylated with alkaline phosphatase using standard techniques widely known in the art and described in detail in Sambrook et at., *Molecular Cloning: A Laboratory Manual*, 2nd Edition. Cold Spring Harbor Laboratory Press (1989). In an exchange reaction, an excess of ADP (adenosine diphosphate) is used to drive an exchange of a 5'-terminal phosphate from the sequence specific oligonucleotide to ADP which is followed by the transfer of $^{32}P$ from $\gamma^{32}P$-ATP to the 5'-end of the oligonucleotide. This reaction is also catalyzed by T4 polynucleotide kinase and is described in Sambrook et al., *Molecular Cloning: A Laboratory Manual*, 2nd Edition. Cold Spring Harbor Laboratory Press (1989).

Homopolymeric tailing is another standard labeling technique useful in the labeling of CviJI* -generated sequence specific oligonucleotides. This reaction involves the addition of hu 32P-labeled nucleotides to the 3'-end of the sequence specific oligonucleotides using a terminal deoxynucleotide transferase. (Sambrook et al., *Molecular Cloning: A Laboratory Manual*, 2nd Edition. Cold Spring Harbor Laboratory Press (1989)).

Commonly used labeling techniques typically employ a single oligonucleotide directed to a single site on the target DNA and containing one or a few labels. Oligonucleotides generated by the method of the present invention are directed to many sites of a target DNA by virtue of the fact that they are generated from a sample of the target sequence. Thus, the hybridization of multiple oligonucleotides (labeled by the methods described above) allows a significantly enhanced sensitivity in the detection of target sequences. In addition, the short length of the labeled oligonucleotides used in the methods of the present invention allows a reduction in hybridization time from overnight (as is used in conventional methods) to 60 mins.

Although labeling sequence specific oligonucleotides with hu 32P is described above, labeling with other radionucleotides, and non-radioactive labels is also within the scope of the present invention.

Example 11

Primer Extension Labeling of DNA Using Restriction-Generated Oligonucleotides (PEL-RGO)

Another aspect of the present invention includes methods for labeling DNA which include the generation of oligonucleotide primers by complete digestion with CviJI*, followed by heat denaturation. PEL-RGO requires three steps: 1) generating the sequence-specific oligonucleotides by CviJI* restriction of the template DNA; 2) denaturation of the template and primer; and primer extension in the presence of labeled nucleotide triphosphates. Plasmid DNA may be prepared by methods known in the art such as the alkaline lysis or rapid boiling methods (Sambrook et at., *Molecular Cloning: A Laboratory Manual*, 2nd Edition). Cold Spring Harbor Laboratory Press, Cold Spring Harbor, N.Y. (1989)). In addition, the vector should be linearized to ensure effective denaturation. A restriction fragment may be labeled after separation on low melting point agarose gels by methods well known in the art.

In PEL-RGO labeling, template DNA to be labeled is divided into two aliquots; one is used to generate the sequence specific oligonucleotide primers and the other aliquot is saved for the primer annealing and extension reaction. A typical reaction mix for generating sequence-specific oligonucleotides is assembled in a microcentrifuge tube and includes: 100 ng DNA; 2 µl 5× CviJI* buffer; 0.5 µl CviJI (1u/µl); sterile distilled water to 10 µl final volume. CviJI* 5× restriction buffer includes: 100 mM glycylglycine (Sigma, St. Louis, Mo., Cat. No. G2265) pH adjusted to 8.5 with KOH, 50 mM magnesium acetate (Amresco, Solon, Ohio, Cat. No. P0013119), 35 mM β-mercaptoethanol (Mallinckrodt, Paris, Ky., Cat. No. 60-24-2), 5 mM ATP, 100 mM dithiothreitol (Sigma, St. Lous, Mo., Cat. No. D9779) and 25% v/v DMSO, (Mallinckrodt Cat. No. 67-68-5). CviJI is obtained from CHIMERx (Madison, Wis.). The reaction mix is incubated at 37° C. for 30 min, followed by the inactivation of CviJI by heating at 65° C. for 10 min. The CviJI*-restricted DNA may be used directly without further purification, or it may be stored at −20° C. for several months for subsequent labeling reactions.

After heat-inactivating CviJI, 0.2 µg of the digested and undigested DNA are electrophoresed on a 1.5% agarose gel, using a suitable molecular weight marker for comparison. The CviJI restriction fragments appear as a low molecular weight smear in the 20–200 bp range.

By way of example, 1–10 ng of linearized pUC19 was labeled under the conditions described below. A template-primer cocktail was prepared by mixing 10 ng of linearized pUC19 DNA template with 20 ng pUC19 sequence-specific oligonucleotides (prepared as described above) and the mixture is brought to a final volume of 17 µl with sterile distilled water. The template-primer mixture is denatured in a boiling water bath for 2 minutes and immediately placed on ice.

The following labeling mixture is then added to the template-primer mix: 2.5 µl 10× labeling buffer (500 mM Tris HCl at pH 9.0, 30 mM MgCl$_2$, 200 mM (NH$_4$)$_2$SO$_4$, 20 µM dATP, 20 µM dTTP, 20 µM dGTP, 0.4% NP-40); 5.0 µl [α-$^{32}$P] dCTP (3000 Ci/mmol, 10 µCi/µl New England Nuclear, Catalog No. NEG013H); 0.5 µl *Thermus flavus* DNA polymerase (5 u/µl) (Molecular Biology Resources, Milwaukee, Wis.); up to 25 µl final volume with distilled water. The reaction was incubated at 70° C. for 30 rain and then stopped by adding 2 µl of 0.5M EDTA at pH 8.0 to the reaction mix.

The efficiency of the labeling reaction is gauged by the percentage of radioisotope incorporated into labeled DNA. One microliter of the labeling reaction is added to 99 µl of 10 mM EDTA in a microcentrifuge tube. This serves as the source of diluted probe for total and trichloroacetic acid (TCA)-precipitable counts. 2 µl of diluted probe is spotted onto the center of a glass fiber filter disc (Whatman number 934-AH). The disc is then allowed to dry and is then placed in a vial containing scintillation cocktail for counting total radioactivity in a liquid scintillation counter. Another 2 µl aliquot from the diluted probe is added to 1 ml of 10% ice cold TCA followed by the addition of 2 µl of carrier bovine serum albumin (BSA). This mixture was then placed on ice for 10 minutes. The precipitate is then collected on a glass filter disc (Whatman No. 934-AH) by vacuum filtration. The filter is then washed with 20 ml of ice cold 10% TCA, allowed to dry and is placed in a vial containing scintillation cocktail and counted.

Because primer extension oligonucleotide labeling results in net DNA synthesis, the specific activity of labeled DNA is calculated using the following guidelines.

Total cpm incorporated=TCA cpm×50×27

Wherein the factor 50 is derived from using 2 µl of a 1:100 dilution for TCA precipitation. The number 27 converts this back to the total reaction volume (which is the reaction volume plus 2 µl of stop solution).

Synthesized DNA (ng of DNA synthesized)=theoretical yield×fraction of radioactivity incorporated.

Theoretical yield (ng of DNA) =

$$\frac{\mu\text{Ci dNTPs added} \times 4 \times 330 \text{ ng/nmole}}{\text{specific activity dNTP(Ci/mmole} = \mu\text{Ci/nmole)}}$$

Fraction of incorporated label=TCA precipitated cpm/total cpm.

Specific activity (cpm/µg of DNA) =

$$\frac{\text{total cpm incorporated} \times 1000}{\text{synthesized DNA + input DNA}}$$

Wherein 1000 is the factor converting nanograms to micrograms.

By way of example, the following represents the calculation of specific activity for an aliquot of pUC19 DNA labeled using this method. Using 50 µCi of [α-$^{32}$P]dCTP in a 25 µl reaction, and if the TCA precipitated cpm is 26192 and total cpm is 102047;

Total cpm incorporated=26192×50×27=3.27×10$^7$ cpm

Synthesized DNA (ng of DNA synthesized)=Theoretical yield×fraction of radioactivity incorporated.

$$\begin{aligned}
\text{Theoretical yield} &= \frac{\mu\text{Ci of dNTPs} \times 4 \times 330}{3000 \ \mu\text{Ci/nmole}} \\
&= \frac{50 \ \mu\text{Ci} \times 4 \times 330}{3000} \\
&= 22 \text{ ng}
\end{aligned}$$

Fraction of label incorporated =

$$\frac{\text{TCA precipitated cpm}}{\text{Total cpm}} = \frac{26192}{102047} = 0.256$$

$$\begin{aligned}
\text{Synthesized DNA} &= 22 \times 0.256 \\
&= 5.6 \text{ ng}
\end{aligned}$$

Specific activity (cpm/µg) = $\frac{\text{Total cpm incorporated}}{\text{Synthesized DNA + input DNA}}$ Input DNA = 10 ng $$\text{Specific activity} = \frac{3.27 \times 10^7 \times 1000}{5.6 + 10}$$

$$= 2.09 \times 10^9 \text{ cpm/}\mu g$$

Unincorporated radioactive label may be removed using standard methods well known in the art.

Comparisons were undertaken between PEL-RGO vs RPL under similar conditions, and it was observed that a detection limit of 100 fg was seen using PEL-RGO labeled DNA compared to a detection limit of 500 fg with RPL, using a radiolabeled probe.

Example 12

Thermal Cycle Labeling

Thermal Cycle Labeling (TCL) is a method according to the present invention for efficiently labeling double-stranded DNA while simultaneously amplifying large amounts of the labeled probe. TCL of DNA requires two general steps: 1) generation of the sequence-specific oligonucleotides by CviJI* restriction of the template DNA; and 2) repeated cycles of denaturation, annealing, and extension in the presence of a thermostable DNA polymerase. Optimal results are obtained after 20 such cycles, which is best performed in an automated thermal cycling instrument such as a Perkin-Elmer Model 480 thermocycler. In conjunction with such an instrument, about 1 hr. is required to complete this protocol. If a thermal cycler is not available these reactions may be performed using heat blocks. As few as 5 cycles may yield probes with acceptable detection sensitivities.

Non-radioactive labeling of DNA using TCL is accomplished by mixing: 10 ng linearized template, 50 ng CviJI*-digested primers (prepared as described above), 1.5 µl 10× labeling buffer, 0.5 µl *Thermus flavus* DNA polymerase (5u/µl) (Molecular Biology Resources, Inc., Milwaukee, Wis.), 1 µl of 1 mM Biotin-11-dUTP (Enzo Diagnostics, New York, N.Y.), 1.5 µl each of dATP, dCTP, and dGTP (2 mM), and 1.0 µl 12 mM dTTP.

Radioactive labeling of DNA using TCL was accomplished by mixing 10–20 ng of CviJI generated primers, 10 pg–25 ng of linearized template, 1.5 µl of 10× labeling buffer, 2.5 µl of $^{32}$P-dCTP (3000 Ci/mmole, 10 µCi/µl or 40 µCi/µl), 0.5 µl of *Thermus flavus* DNA polymerase (5u/µl), and 0.5 µl each of dATP, dGTP, and dTTP (1 mM) was added. The reaction mix was brought to a volume of 15 µl with deionized H$_2$O, overlaid with mineral oil and cycled through 20 rounds of denaturation, annealing and extension. A typical cycling regimen employed 20 cycles of denaturation at 91° C. for 5 sec, annealing at 50° C. for 5 sec and extension at 72° C. for 30 sec. The reaction is then terminated by adding 1 µl of 0.5M EDTA, pH 8.0. The amplified, labeled probe is a very heterogeneous mixture of fragments, which appears as a smear when analyzed by agarose gel electrophoresis.

Estimation of Bio-11 dUTP Incorporation

In order to estimate the level of incorporation of biotin-11-dUTP into DNA, a serial dilution from 1:10 to 1:10$^8$ of the labeled probe (free of unincorportated biotin-11-dUTP) is made in TE (10 mM Tris, 1 mM EDTA, pH 8). A microliter of each dilution is placed on a neutral nylon membrane, and the DNA sample is bound to the membrane either by UV cross linking for 3 min or by baking at 80° C. for 2 hr.

The unbound sites on the membrane are blocked using a blocking buffer for 15 rain at 25° C. Streptavidin-alkaline phosphatase (Gibco-BRL Gaithersburg, Md., Cat. No. 9545A) is added to the blocking buffer (0.058 M Na$_2$HPO$_4$, 0.017M NaH$_2$PO$_4$, 0.068M NaCl, 0.02% sodium azide, 0.5% casein hydrolysate, 0.1% Tween-20) at a 1:5000 dilution and incubated for a 30 min., and the membrane is rinsed 3 times for 10 min. each with wash buffer (1× PBS [0.058M Na$_2$HPO$_4$, 0.017M NaH$_2$PO$_4$, 0.068M NaCl], 0.3% Tween, 0.2% sodium azide), rinsed briefly (5 minutes) with AP buffer (100 mM NaCl, 5 mM MgCl$_2$, 100 mM Tris-Cl pH 9.5) and then enough AP buffer containing 4.0 µl/ml nitro blue tetrazolium (NBT) (Sigma Cat. No. N6639), (Sigma Cat. No. B6777), and 3.5 µl/ml of 5-bromo-4-chloro-3-indolyl phosphate (BCIP) was added in order to cover the membrane. The membrane is left in the dark for approximately 30 minutes or until the reaction is complete. The reaction is stopped by rinsing in 1× PBS.

Detection Sensitivities $^{32}$P-labeled probes generated by the TCL protocol detect as little as 25 zeptomoles (2.5×10$^{-20}$ moles) of a target sequence. As little as 10 pg of template DNA is enough to synthesize 5–10 ng of radiolabeled probe, which is sufficient for screening 5 Southern blots. This radioactive version of TCL facilitates extremely high specific activities of labeled probe (1–2×10$^{10}$ cpm/µg DNA), which permits 5–10 fold lower detection limits than conventional labeling protocols. The synthesis of higher specific activity probes is probably the net result of the sequence- specific oligonucleotide primers and their increased length when compared to the short random primers used in other labeling methods. In addition, the thermal cycling permits probe amplification.

Biotin-labeled probes generated by the TCL protocol detect as little as 25 zeptomoles (2.5×10$^{-20}$ moles) of a target sequence. A 50 µl TCL reaction yields as much as 25 µg of labeled DNA, enough to probe 25 to 50 Southern blots. Biotin-labeled TCL probes provide a 10 fold greater detection sensitivity compared to RPL biotin probes. In addition, the thermal cycling permits probe amplification.

Non-radioactive, biotinylated probes labeled by the TCL method were shown to have detection limits that are identical to the radioactive probes. This method has an advantage of eliminating the need to work with hazardous radioactive materials without sacrificing sensitivity. In addition, results are obtained from non-isotopic probes in 3–4 hours compared to 3–4 days for radiolabeled probes. The ability to substitute non-radioactive probes for radioactive probes may be very useful to clinical laboratories, which do not use radioisotopes but do need greater detection sensitivities. Research laboratories favor the use of non-isotopic systems if detection sensitivity is not an issue. The non-isotopic labeling version of the TCL system represents a major improvement in labeling DNA probes. Non-radioactive probes generated by the methods of the present invention are also useful in the detection of RNA in situ. An advantage of this system is that RGO labeling yields highly sensitive, non-radioactive probes, and the size of the probes are predominantly in the small molecular weight range and can therefor penetrate the tissue easily, unlike RPL. Because non-radioactive probes labeled using RGO labeling have the same detection limits as do radioactive probes similarly labeled, it is within the scope of this invention to use either radioactive or non-radioactive probes for probing, for example, Southern blots, Northern blots, and for in situ hybridization for the detection of mRNA in cells or tissue directly.

Example 13

Quasi-Random Fragmentation of DNA

Shotgun cloning and sequencing requires the generation of an overlapping population of DNA fragments. Therefore, conditions were established for the partial digestion of DNA with CviJI to produce an apparently random pattern, or smear, of fragments in the appropriate size range. Conventional methods for obtaining partially restricted DNA include limiting the incubation time or limiting the amount of enzyme used in the digestion. Initially, agarose gel electrophoresis and ethidium bromide staining of the treated DNA were utilized to assess the randomness and size distribution of the fragments.

Figure 7:
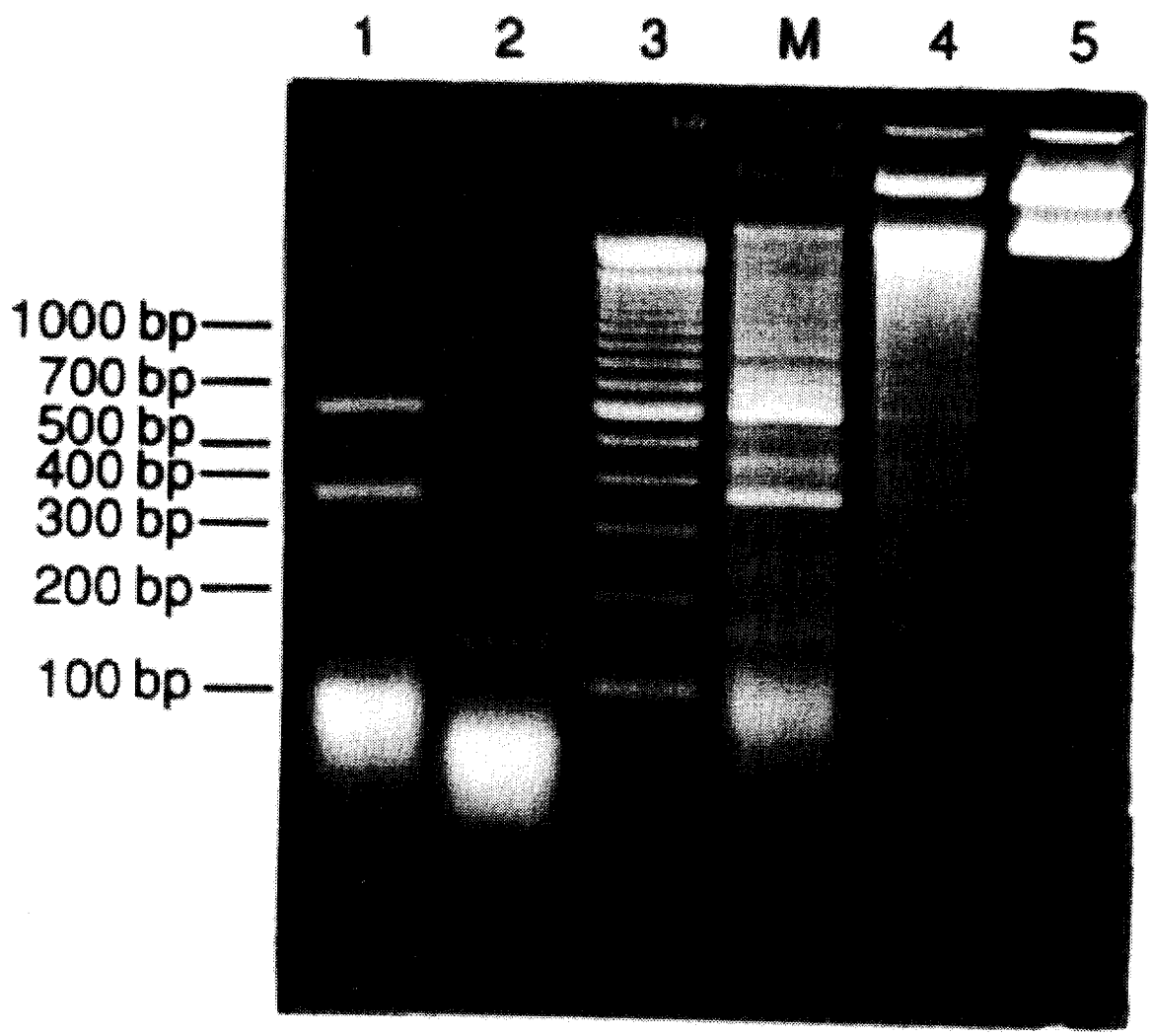
FIG. 7 is a photographic reproduction of a gel depicting CviJI restriction digests of pUC19.

CviJI was obtained from CHIMERx (Madison, Wis.). Digestion of pUC19 DNA for limited time periods, or with limiting amounts of CviJI under normal or relaxed conditions, did not produce a quasi-random restriction pattern, or smear. Instead, a number of discrete bands were observed, as shown in FIG. 7, lane 3 for the CviJI* partial digestion of pUC19. Complete digests of pUC19 under normal and CviJI* buffer conditions are shown in lanes 1 and 2 respectively. These results show that, under these relaxed conditions, CviJI has a strong restriction site preference.

To eliminate the apparent restriction site preferences observed under the partial restriction conditions described above, a series of altered reaction conditions were explored. Conditions of high pH, low ionic strength, addition of solvents such as glycerol or dimethylsulfoxide, and/or substitution of $Mn^{2+}$ for $Mg^{2+}$ were systematically tested with CviJI endonuclease using the plasmid pUC19. FIG. 7 shows the results of these tests. In Lane M, a 100 bp DNA ladder was run. In Lanes 1–4, pUC19 DNA (1.0 µg) was run after digestion at 37° C. in a 20 µl volume for the following times and conditions: Lane 1, complete CviJI digest (1 unit of enzyme for 90 min in 50 mM Tris-HCl, pH 8.0, 10 mM $MgCl_2$, 50 mM NaCl); Lane 2, complete CviJI* digest (1 unit of enzyme for 90 min in 50 mM Tris-HCl, pH 8.0, 10 mM $MgCl_2$, 50 mM NaCl, 1 mM ATP, 20 mM DTT); Lane 3, partial CviJI* digest (0.25 units of enzyme for 30 min in 50 mM Tris-HCl, pH 8.0, 10 mM $MgCl_2$, 50 mM NaCl, 1 mM ATP, 20 mM DTT); Lane 4, partial CviJI** digest (0.5 units of enzyme for 60 min in 10 mM Tris-HCl, pH 8.0, 10 mM $MgCl_2$, 10 mM NaCl, 1 mM ATP, 20 mM DTT, 20% v/v DMSO); and Lane 5, uncut pUC19 (1.0 µg).

The digestion condition which yielded the best "smearing" pattern was obtained when the ionic strength of the relaxed reaction buffer was lowered and an organic solvent was added (FIG. 7, lane 4). Plasmid pUC19 partially digested under these conditions yields a relatively non-discrete smear. This activity is referred to as CviJI** to differentiate it from the originally-characterized star activity described in Xia et al., *Nucl. Acids Res.* 15:6075–6090 (1987). The appearance of diffuse, faint bands overlying a background smear generated from this 2686 bp molecule indicates that some weakly preferred or resistant restriction sites may bias the results of subsequent cloning experiments.

DNA was mechanically sheared by sonication utilizing a Heat Systems Ultrasonics (Farmingdale, N.Y.) W-375 cup horn sonicator as specified by Bankier et al., *Methods in Enzymology* 155:51–93 (1987). DNA fragmented by this method has random single-stranded overhanging ends (ragged ends).

CviJI* digested and sonicated samples were size fractionated by agarose gel electrophoresis and electroelution, or by spin columns packed with the size exclusion gel matrix, Sephacryl S-500 (Pharmacia LKB, Piscataway N.J.) to eliminate small DNA fragments. Spin columns (0.4 cm in diameter) were packed to a height of 1.3 cm by adding 1 ml of Sephacryl S-500 slurry and centrifuging at 2000 RPM for 5 minutes in a Beckman CPR centrifuge. The columns were rinsed 3 times with 1 ml aliquots of 100 mM Tris-HCl (pH 8.0) by centrifugation at 2000 RPM for 2 min. Typically, 0.2–2.0 µg of fragmented DNA in a total volume of 30 µl was applied to the column. The void volume, containing those DNA fragments larger than 500 bp, was recovered in the column eluant after spinning at 2000 RPM for 5 minutes. The capacity of this micro-column procedure is 2 µg of DNA. Agarose gel electrophoresis and electroelution are described in detail by Sambrook et al. *Molecular Cloning: A Laboratory Manual*, Second Edition Cold Spring Harbor Laboratory Press, Cold Spring Harbor, N.Y. (1989) and is well known to those skilled in the art. In these experiments, 5 µg of sample was pipetted into a 2 cm-wide slot on a 1% agarose gel. Electrophoresis was halted after the bromophenol blue tracking dye had migrated 6 cm. Fragments larger than 750 bp, as judged by molecular size markers, were separated from smaller sizes and electrophoresed onto dialysis tubing (1000 MW cutoff). The fractionated material was extracted with phenol-chloroform and precipitated using ice cold ethanol (50% final volume) and ammonium acetate (2.5M final concentration).

The ragged ends of the sonicated DNA were rendered blunt utilizing two different end repair reactions. In one end repair reaction (ER 1) sonicated DNA was treated according to the procedure outlined by Bankier et al. *Methods in Enzymology* 155:51–93 (1987), where 2.0 µg of sonicated lambda DNA is combined with 10 units of the Klenow fragment of DNA polymerase I, 10 units T4 DNA polymerase, 0.1 mM dNTPs, (deoxynucleotide triphosphates= deoxyadenosine triphosphate, deoxthymidine triphosphate, deoxycytosine triphosphate, and deoxyguanosine triphosphate) and reaction buffer (50 mM Tris-HCl, pH 7.5, 10 mM $MgCl_2$, 10 mM DTT). This mixture was incubated at room temperature for 30 min followed by heat denaturation of the enzymes at 65° C. for 15 minutes. In a second end repair reaction (ER 2), an excess of the reagents and enzymes described above were utilized to ensure a more efficient conversion to blunt ends. In this reaction, 0.2 µg of the sonicated lambda DNA sample was treated under the same reaction conditions described above.

Figure 8:
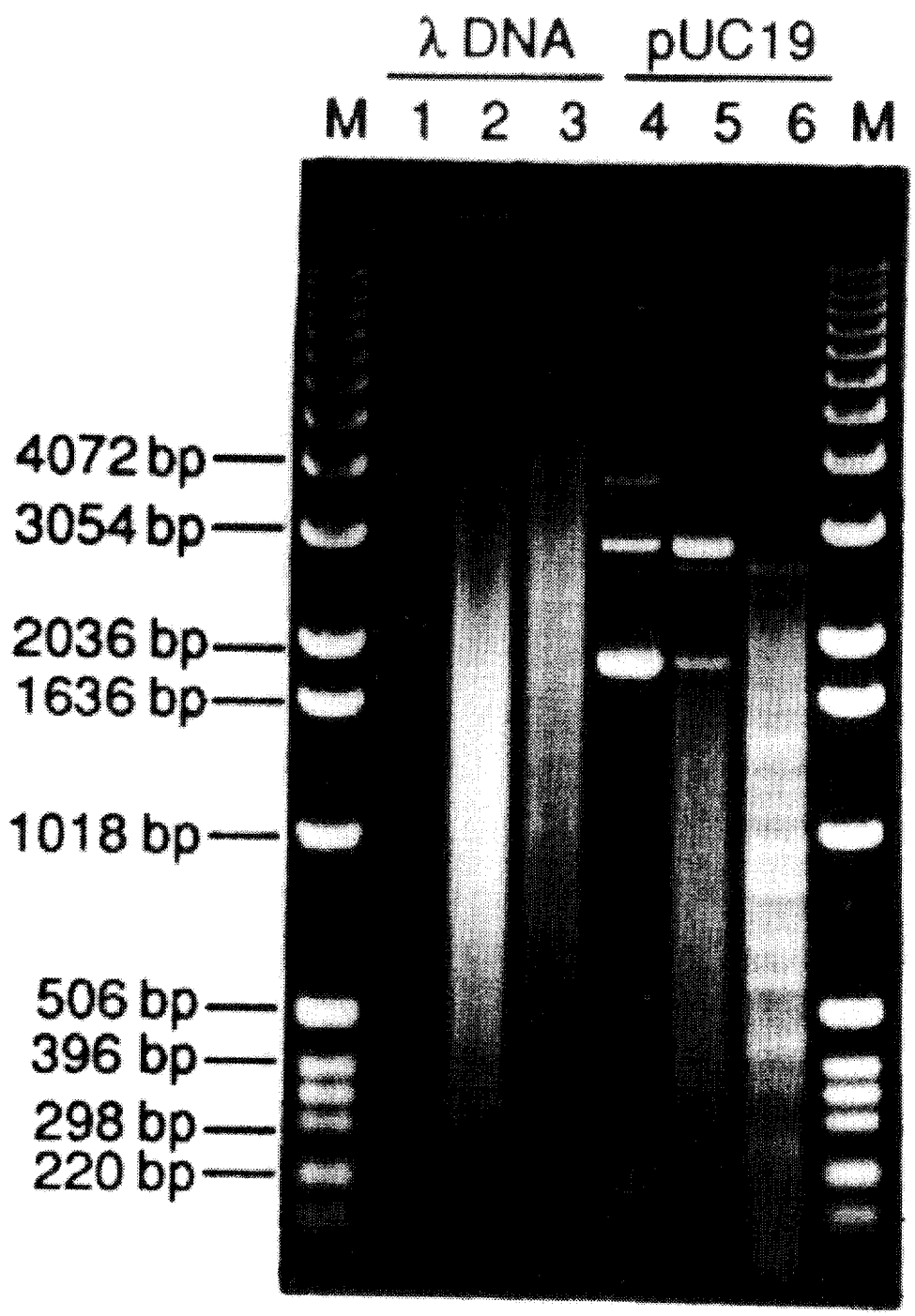
FIG. 8 is a photographic reproduction of a gel depicting comparisons of sonicated versus CviJI* partially digested DNAs.

FIG. 8 shows comparisons of the size distributions of sonicated DNA versus DNA that was partially digested with CviJI. In Lanes M, a 1 kb DNA ladder was run. In Lanes 1–3, untreated λ DNA (0.25 µg), sonicated λ DNA (1.0 µg), and CviJI partially-digested λ DNA (1.0 µg) were run, respectively. In Lanes 4–6, untreated pUC19 (0.25 µg), sonicated pUC19 (1.0 µg), and CviJI** partially-digested pUC19 (1.0 µg) were run, respectively.

Fragmentation of a large substrate such as lambda DNA (45 kb) revealed essentially no banding differences between the CviJI method and sonication, as demonstrated in FIG. 8, lanes 2 and 3. In addition, pUC19 DNA that was partially digested with CviJI gave a size distribution or "smear" that closely resembled that achieved with sonication (FIG. 8, lanes 5 and 6). As expected, the minor bias evident with a small molecule such as pUC19 was not detectable with a larger substrate such as lambda DNA.

The intensity and duration of sonic treatment affects the size distribution of the resulting DNA fragments. The results obtained from the sonication of lambda and pUC19 samples (FIG. 8) were obtained from three 20 second pulses at a power setting of 60 watts. Sonication-generated smears are similar, although the size distribution of fragments is consistently greater with CviJI** fragmentation. This result favors the cloning of larger inserts, which facilitates the efficiency of end-closure strategies (Edwards et al., *Genome* 6:593–608 (1990)). The size distribution of the DNA fragmented by CviJI** is controlled by incubation time and amount of enzyme, variables which are readily optimized by routine analysis. An excess of enzyme or a long incubation time will completely digest pUC19 DNA, resulting in fragments which range in size from approximately 20 bp to approximately 150 bp (FIG. 7, lanes 1 and 2). The results shown in FIG. 8 were obtained by incubating pUC19 for 40 minutes and lambda DNA for 60 minutes with 0.33 units of CviJI/ μg substrate. The efficiencies of the two methods for randomly fragmenting DNA were quantitatively analyzed for use in molecular cloning, as described below.

Example 14

Rapid DNA Size Fractionation Utilizing Spin Column Chromatography

The amount of data obtained by the shotgun sequencing approach is substantially increased if fragments of less than 500 bp are eliminated prior to the cloning step. Small fragments yield only a portion of the sequence data which may be collected from polyacrylamide gel based separations and, thus, such small fragments lower the efficiency of this strategy. Agarose gel electrophoresis followed by electroelution is commonly used to size fractionate DNA prior to shotgun cloning (Bankier et al., *Methods in Enzymol.* 158:51–93 (1987)). Approximately three hours are required to prepare the agarose gel, electrophorese the sample, electroelute fragments larger than 500 bp, perform phenol-chloroform extractions, and precipitate the resulting material.

Figure 9A:
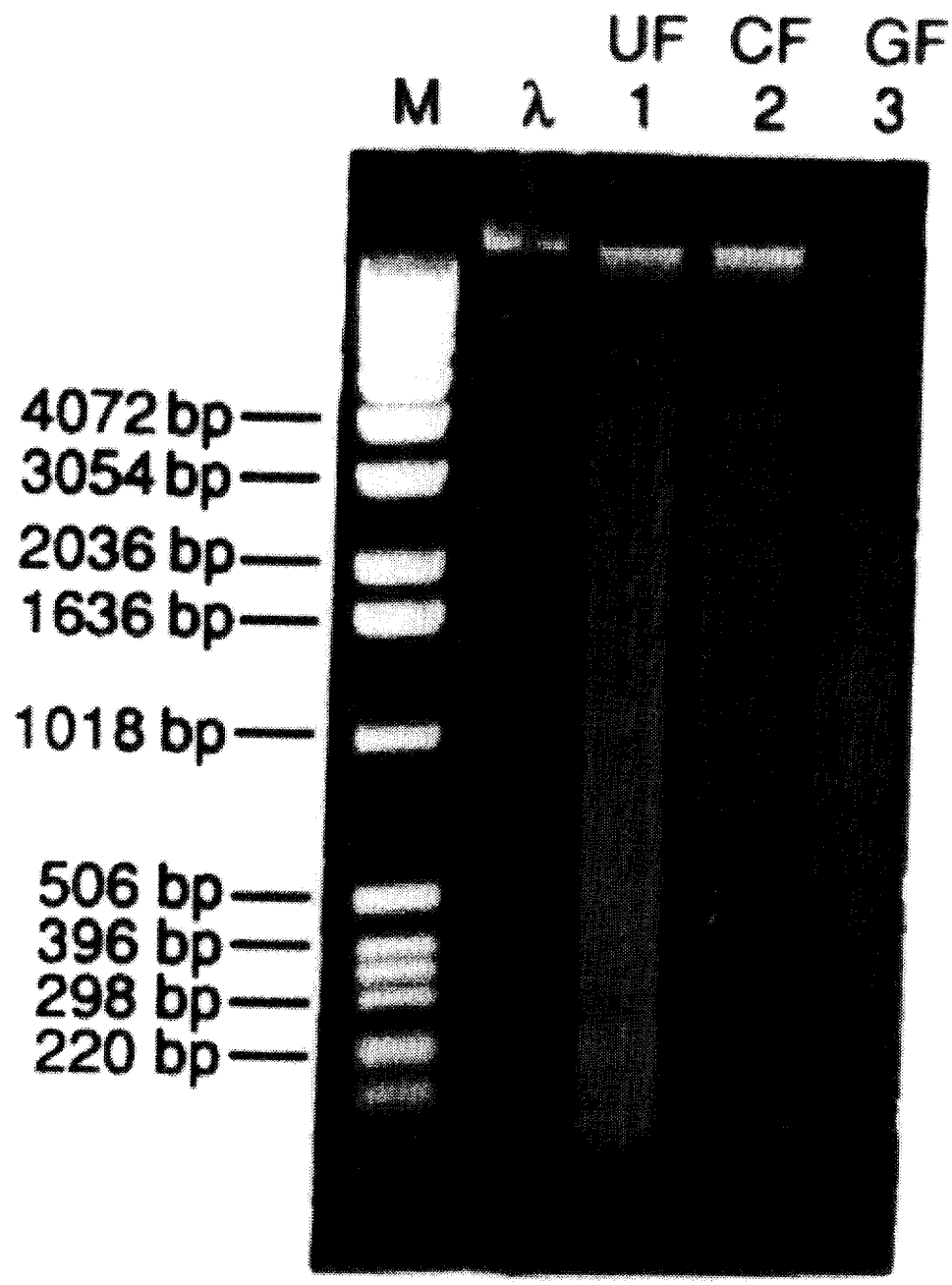
FIG. 9A is a photographic reproduction of an agarose gel electrophoresis analysis of size-fractionated DNA by microcolumn chromatography compared to fractionation by agarose gel electroelution.

The results of 5 out of 9 independent trials size-fractionating CviJI-fragmented lambda DNA by agarose gel electrophoresis are shown in FIGS. 9A–E. FIGS. 9A–D illustrate the following. In FIG. 9A: Lane M, 1 kb DNA ladder; lane λ, untreated λ, DNA (0.25 μg); lane 1, unfractionated (UF) CviJI partially-digested λ DNA (1.0 μg); lane 2, column-fractionated (CF) CviJI partially-digested λ DNA (1.0 μg); lane 3, gel-fractionated (GF) CviJI partially-digested λ DNA (1.0 μg); and in FIGS. 9B–E are additional trials of the same treatments as in the lanes of FIG. 9A which have the same label.

Small DNA fragments may also be removed by passing the sample through a short column of Sephacryl S-500. Approximately 15 min. are needed to prepare the column and 5 min. to fractionate the DNA by this method.

Figure 9B:
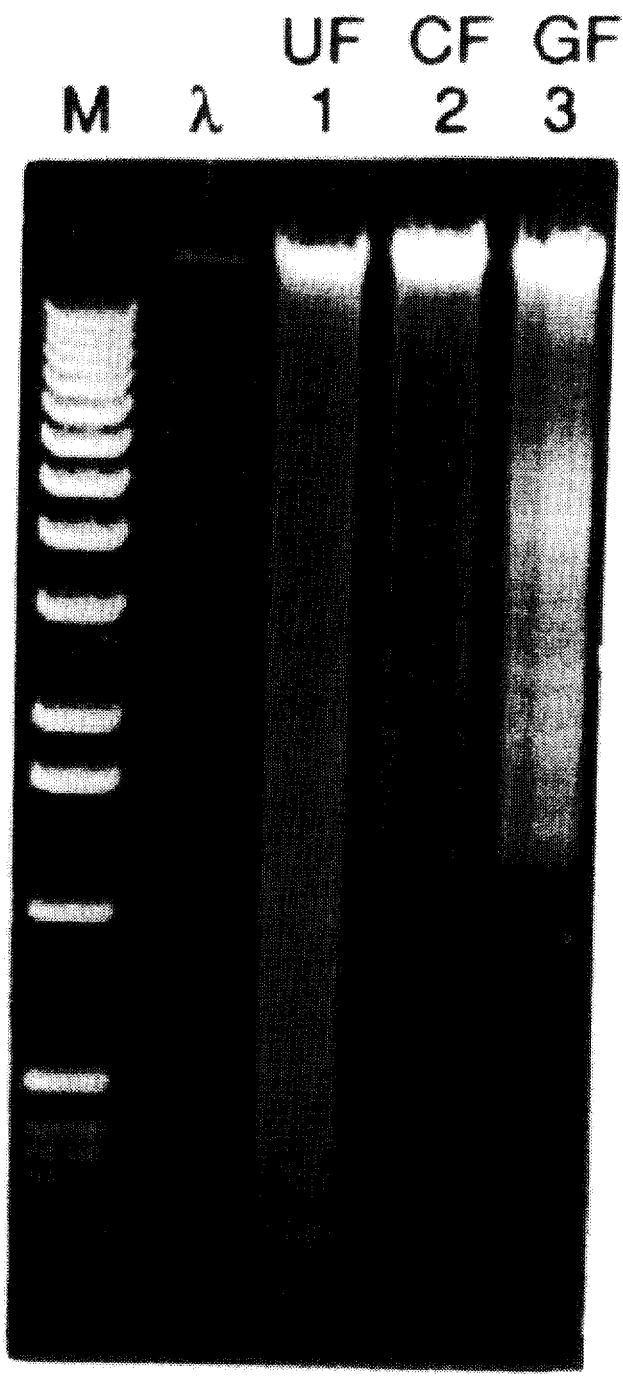
FIG. 9B–E illustrates additional trials of the same procedures used in FIG. 9A.
Figure 9C:
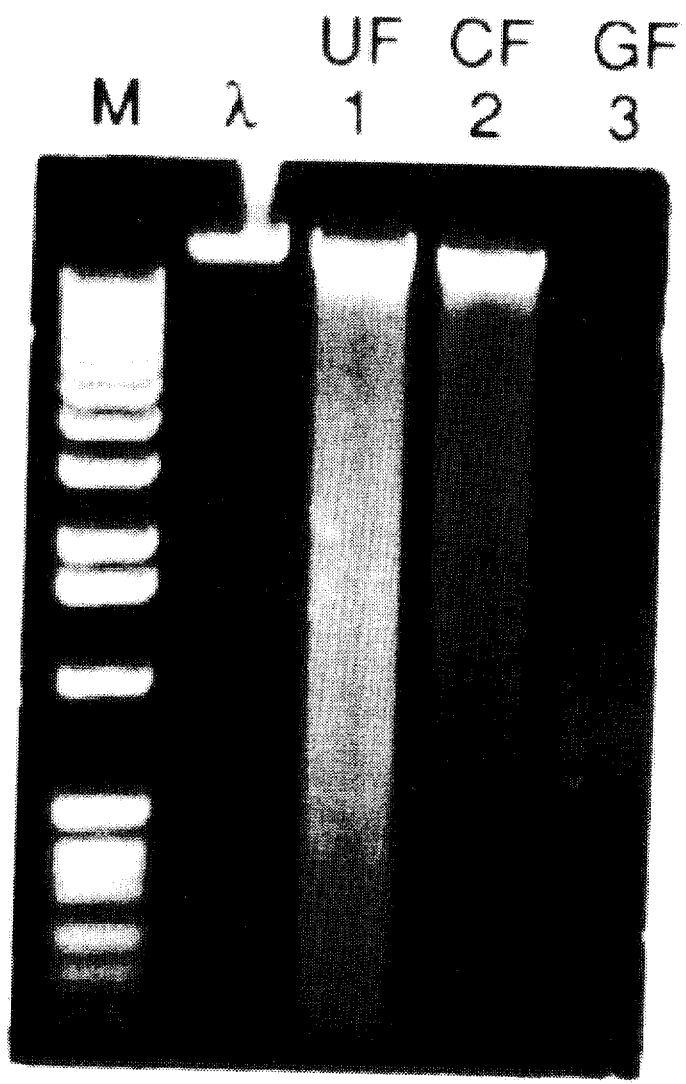
Figure 9D:
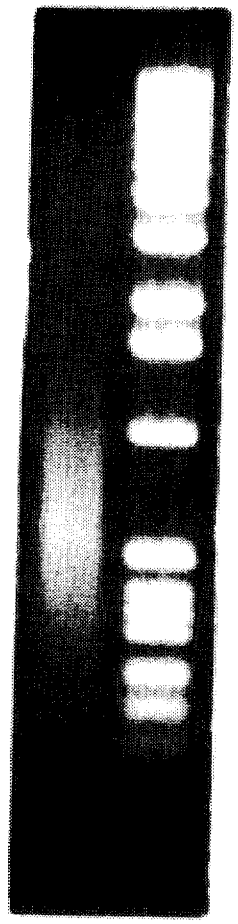
Figure 9E:
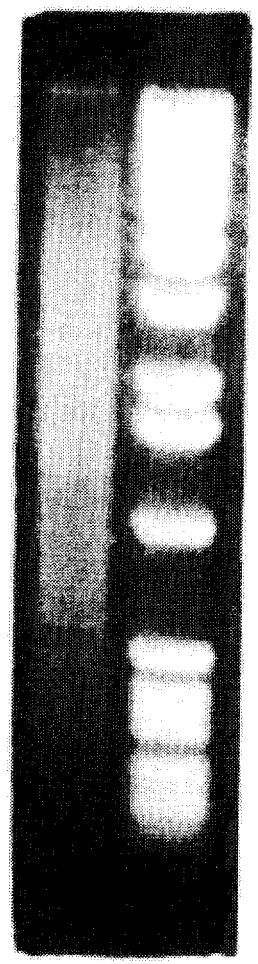

The results of three out of nine trials using a Sephacryl S-500 column are shown in FIGS. 9A–C. The efficiency of eliminating small DNA fragments (<500 bp) by spin column chromatography appears high, and the reproducibility was excellent. This result is in contrast to the agarose gel electrophoresis and electroelution data presented in FIGS. 9A–E wherein nine replicate trials of this method yielded nine differently sized products, regardless of the source of the agarose. Both methods yielded 30–40% recoveries as measured by UV spectrophotometry. To quantitate the relative efficiencies of the two fractionation methods, the lambda DNA size fractionated in FIG. 9A lanes 2 and 3, and FIG. 9B lane 3 were analyzed for cloning efficiency and insert size, as described below.

Example 15

Cloning Efficiencies of Gel Elution and Chromatography Fractionation Methods

The efficacy of size selection was quantified by two criteria: 1) by comparing the relative cloning efficiency of CviJI** partially-digested lambda DNA fragments fractionated either by agarose gel electrophoresis and electroelution or micro-column chromatography, and 2) determining the size distribution of the resulting cloned inserts. To reduce potential variables, large quantities of the cloning vector and ligation cocktail were prepared, ligation reactions and transformation of competent *E. coli* were performed on the same day, numerous redundant controls were performed, and all cloning experiments were repeated twice. Ligation reactions were carded out overnight at 12° C. in 20 μl mixtures using the following conditions: 25 mM Tris-HCl (pH 7.8), 10 mM $MgCl_2$, 1 mM DTT, 1 mM ATP, DNA, and 2000 units of T4 DNA ligase. For unfractionated samples, 10 ng of fragments and 100 ng of HincII-restricted, dephosphorylated pUC19 were combined under the above conditions. For Sephacryl S-500 fractionated samples, 50 ng of size-selected fragments were ligated with 100 ng of HincII-restricted, dephosphorylated pUC19. This increase in fractionated DNA was determined empirically to compensate for the lower concentration of "ends" resulting from the fractionation procedure and/or the lowered efficiency of cloning larger fragments. Ligation reaction products were added to competent *E. coli* DH5αF' (φ80 dlacZΔM15 Δ(lacZYA-argF)U169 deoR gyrA96 recA1 relA1 endA1 thi−1 hsdR17($r_K^-,m_K^+$) supE44 λ−) in a transformation mixture as specified by the manufacturer (Life Technologies, Bethesda, Md.) and aliquots of the transformation mixture were plated on T agar (Messing, *Methods in Enzymol.* 101:20–78 (1983)) containing 20 μg/ml ampicillin, 25 μl of a 2% solution of isopropylthiogalactoside (IPTG) and 25 μl of a 2% solution of 5-dibromo-4-chloro-3-indolylgalactoside (X-GAL). The cloning efficiencies reported are the average of triplicate platings of each ligation reaction. The concentration of the fractionated material was checked spectrophotometrically so that 50 ng was added to all ligation reactions. This material was ligated to HincII-digested and dephosphorylated pUC19. This cloning vector was chosen because it permits a simple blue to white visual assay to indicate whether a DNA fragment was cloned (white) or not (blue) (Messing, *Methods in Enzymol.* 101:20–78 (1983)).

A summary of the cloning efficiencies calculated from two independent trials is given in Table 3.

TABLE 3

Cloning Efficiencies of CviJI** Partially Digested Lambda DNA Fractionated by Microcolumn Chromatography Versus Agarose Gel Electroelution.

| | Trial I | | Trial II | |
|---|---|---|---|---|
| | Colony Phenotype | | | |
| DNA/treatment | Blue | White | Blue | White |
| Supercoiled pUC19 | 55000 | <10 | 50000 | <10 |
| pUC19/HincII/CIAP | 210 | <1 | 320 | 1 |
| pUC19/HincII/CIAP/ T4 DNA ligase | 150 | 4 | 210 | 7 |

TABLE 3-continued

Cloning Efficiencies of CviJI** Partially Digested Lambda DNA Fractionated by Microcolumn Chromatography Versus Agarose Gel Electroelution.

| | Trial I | | Trial II | |
|---|---|---|---|---|
| | Colony Phenotype | | | |
| DNA/treatment | Blue | White | Blue | White |
| λ/CviJI** partial/CF + pUC19 | 140 | 240 | 210 | 240 |
| λ/CviJI** partial/GFE1 + pUC19 | 98 | 49 | 200 | 18 |
| λ/CviJI** partial/GFE2 + pUC19 | 82 | 54 | 95 | 74 |

Cloning efficiencies reflect the number of ampicillin-resistant colonies/ng pUC19 DNA. CIAP represents treatment with calf intestinal alkaline phosphatase used to dephosphorylate HincII-digested pUC19 to minimize self-ligation. CF refers to DNA that was fractionated on Sephacryl S-500 columns as described above. GFE1 and GFE2 refer to two runs wherein DNA was fractionated by agarose gel electrophoresis and electroeluted. λ refers to bacteriophage λ DNA.

These trials represent repeated experiments in which λ DNA fragments generated by CviJI** partial digestion were ligated to HincII-linearized, dephosphorylated pUC19 and transformed into DH5αF' competent cells described above. The first three rows in Table 2 show controls performed to establish a baseline to better evaluate the various treatments. Supercoiled pUC19 transforms *E. coli* 10 times more efficiently than the HincII-digested plasmid and 150–260 times more efficiently than the HincII-digested and dephosphorylated plasmid. The number of blue and white colonies which resulted from transforming HincII-cut and dephosphorylated pUC19 was determined both before and after treatment with T4 DNA ligase in order to differentiate these background events from cloning inserts. The background of blue colonies (which represent the uncut and/or non-dephosphorylated population of molecules) averaged 0.4%, compared to supercoiled plasmid. The background of white colonies (which presumably results from contaminating nucleases in the enzyme treatments or genomic DNA in the plasmid preparations) after HincII-digestion, dephosphorylation, and ligation of pUC19 averaged 0.014% as compared to the supercoiled plasmid.

The number of white colonies obtained when microcolumn fractionated DNA was cloned into pUC19 was 240/ng vector in both trials. The efficiency of cloning gel fractionated and electroeluted DNA ranged from 18–74 white colonies/ng vector. The data show that column fractionated DNA results in three to thirteen times the number of white colonies, and presumably recombinant inserts, as gel fractionated and electroeluted DNA. The size distribution of the inserts present in these white colonies is depicted in FIGS. 10A–C. In FIG. 10A, a CviJI partial digest of 2 μg of λ DNA was size fractionated on a 4 mm by 13 mm column of Sephacryl S-500 at 2,000×g for 5 minutes. The void volume containing partially digested DNA was directly ligated to linear, dephosphorylated pUC19 and 43 resulting clones were analyzed for insert size. The DNA for this experiment is the same as that shown in FIG. 9A, lane 2. In FIG. 10B, a CviJI partial digest of 5 μg of λ DNA was size fractionated by agarose gel electroelution. The eluted DNA was phenol-extracted and ligated to linear, dephosphorylated pUC19, and the resulting 40 clones were analyzed for insert size. The DNA for this experiment is the same as that shown in FIG. 9A, lane 3. In FIG. 10C, the procedure is the same as in FIG. 9B, except the DNA for this experiment came from FIG. 9B, lane 3.

A total of 43 random clones obtained from micro-column chromatography fractionation were analyzed for insert size (as shown in FIG. 10A). Most of these inserts were larger than 500 bp (37/43 or 86%), 11.6% (5/43) were smaller than 500 bp, and one clone (2.3%) was smaller than 250 bp. The average insert size was 1630 bp. These results are in contrast to those obtained by agarose gel fractionation (as shown in FIGS. 10B and 10C). In the first trial (FIG. 10B) most of the inserts were smaller than 500 bp (26/37 or 70.3%) and only 29.7% (11/37) were larger than 500 bp in size. In the second trial (FIG. 10C) all of the inserts (40 total) were smaller than 500 bp. Thus, the use of agarose gel electroelution for the size fractionation of DNA results in unexpectedly variable and low cloning efficiencies.

Example 16

Cloning Sonicated and CviJI**-Digested Lambda DNA

To compare the cloning efficiencies of sonicated and CviJI**-digested nucleic acid, λ DNA was fragmented by each of these methods and ligated to pUC19 which was linearized with HincII and dephosphorylated to minimize self-ligation.

DNA fragmented by CviJI** digestion and sonication was cloned both before and after Sephacryl S-500 size fractionation. Sonicated lambda DNA was subjected to an end repair treatment prior to ligation. Ligations were performed as described in Example 11. One-tenth of the ligation reaction (2 μl) was utilized in the transformation procedure, and the fraction of nonrecombinant (blue) versus recombinant (white) colonies was used to calculate the efficiency of this process.

The efficacy of the methods was quantified by comparing the cloning efficiency of lambda DNA fragments generated either by sonication or CviJI partial digestion. To reduce potential cloning differences based on size preference, the size distribution of the DNA generated by these two methods was closely matched. Other experimental details were designed to reduce potential variables, as described above. Certain variables were unavoidable, however. For example, the sonicated DNA fragments required an enzymatic step to repair the ragged ends as described in Example 1 prior to ligation, whereas the CviJI digests were heat-denatured and directly ligated to HincII digested pUC19.

A summary of the cloning efficiencies calculated from two independent trials is given in Table 4, section A (unfractionated samples), and Section B (fractionated samples).

TABLE 4

Cloning Efficiencies of CviJI** Digested λ DNA Versus Sonicated λ DNA

| | Trial I | | Trial II | |
|---|---|---|---|---|
| | Colony Phenotype | | | |
| DNA/treatment | Blue | White | Blue | White |
| A. Unfractionated Samples | | | | |
| Supercoiled pUC19 | 30000 | <10 | 16000 | <10 |
| pUC19/HincII/CIAP | 150 | <1 | 31 | 1 |
| pUC19/HincII/CIAP/ T4 DNA ligase | 100 | <1 | 15 | 1 |
| λ/AluI + pUC19 | 200 | 400 | 73 | 250 |
| λ/CviJI** Partial + pUC19 | 100 | 160 | 97 | 340 |
| λ/Sonicated + pUC19 | — | — | 11 | 29 |

TABLE 4-continued

Cloning Efficiencies of CviJI** Digested λ DNA Versus Sonicaled λ DNA

|  | Trial I | | Trial II | |
| --- | --- | --- | --- | --- |
|  | Colony Phenotype | | | |
| DNA/treatment | Blue | White | Blue | White |
| λ/Sonicated/ER 1 + pUC19 | 17 | 10 | 10 | 44 |
| λ/Sonicated/ER 2 + pUC19 | — | — | 40 | 100 |
| B. Frationated Samples | | | | |
| Supercoiled pUC19 | 35000 | <10 | 12000 | <10 |
| pUC19/HincII/CIAP | 30 | <1 | 180 | <1 |
| pUC19/HincII/CIAP/ T4 DNA ligase | 60 | <1 | 10 | <1 |
| λ/AluI + pUC19 | 28 | 23 | 33 | 48 |
| λ/CviJI** Partial + pUC19 | 31 | 90 | 36 | 68 |
| λ/Sonicated + pUC19 | 20 | 6 | 99 | 19 |
| λ/Sonicated/ER 1 + pUC19 | 27 | 32 | 40 | 19 |
| λ/Sonicated/ER 2 + pUC19 | — | — | 25 | 63 |

Cloning efficiencies represent the number of ampicillin-resistant colonies/ng pUC19 DNA. CIAP indicates treatment with calf intestinal alkaline phosphatase. ER 1 and ER 2 are end repair methods described in Example 13. λ refers to bacteriophage lambda.

The indicated trials represent repeated experiments in which two identical sets of lambda DNA fragments generated by AluI complete digestion, CviJI partial digestion, or sonication were each ligated to HincII-linearized, dephosphorylated pUC19 and transformed into DH5αF' competent cells. The cloning efficiencies reported are the average of triplicate platings of each ligation reaction. In case the Sephacryl S-500 size fractionation step introduced inhibitors of ligation or transformation or resulted in differences attributable to the size of the material, the sonicated and CviJI-digested samples were ligated with pUC19 both prior to (A) and after (B) the fractionation steps. The first three rows in Table 4, sections A and B, are controls performed to establish a baseline to better evaluate the various treatments. These data show that supercoiled pUC19 transforms $E.$ $coli$ 200–1000 times more efficiently than the HincII-restricted and dephosphorylated plasmid. Without this dephosphorylation step, the cloning efficiency is 10% that of the supercoiled molecule (data not presented). The background of blue colonies averaged 0.5% in these experiments, compared to supercoiled plasmid, while the background of white colonies averaged 0.005%.

A comparison of the data from unfractionated versus fractionated samples in Table 4, sections A and B, reveals a general decline in the number of white and blue colonies obtained after sizing. This decrease is primarily due to the fact that cloning efficiencies are dependent upon the size of the fragment, favoring smaller fragments and thus giving higher efficiencies for the unfractionated material. This is illustrated by comparing the efficiency of cloning unfractionated and fractionated λ DNA which was completely restricted with AluI. This four base recognition endonuclease produces blunt ends and cuts λ DNA (48,502 bp) at 143 sites. Only 25 of the resulting 144 fragments (17%) are larger than 500 bp. The number of white colonies obtained when unfractionated λ DNA, completely restricted with AluI, was cloned into pUC19 ranged from 250–400/ng vector, versus 23–48/ng vector for the fractionated material. This ten fold decrease was only noticed for the λ Alu I digests, and probably reflects the large portion of small molecular weight fragments (approximately 75%) which is excluded from the fractionated ligation reactions.

The number of white colonies obtained when unfractionated CviJI treated λ DNA was cloned into pUC19 ranged from 160–340/ng vector, versus 68–90 white colonies/ng vector if the same material was fractionated. Unfractionated λ DNA, completely digested with AluI, results in cloning efficiencies very similar to unfractionated CviJI treated DNA. Sonicated λ DNA is a poor substrate for ligation, compared to CviJI** treatment, as indicated by the roughly ten-fold reduced cloning efficiencies.

Enzymatic repair of the ragged ends produced by sonication results in an increased cloning efficiency. Using conditions described in Example 13 for the first end repair treatment (ER 1), 10–44 (fractionated) and 19–32 (unfractionated) white colonies/ng vector were observed. However, ER 1 conditions may not be optimal, as an alternate end repair reaction (ER 2) (as described in Example 13) resulted in greater numbers of white colonies (63 and 100/ng vector for fractionated and unfractionated DNA, respectively). In this reaction, a ten-told excess of reagents and enzymes were utilized to repair the sonicated DNA, which apparently improved the efficiency of cloning such molecules by two to three fold. The data collected from multiple cloning trials in Table 3, sections A and B, show that CviJI partial digestion results in three to sixteen times the number of white colonies than sonicated ER 1-treated DNA. Even with an optimal end repair reaction for the sonicated fragments, DNA treated with CviJI yielded three times more white colonies.

Example 17

Analysis of CviJI** Fragmentation for Shotgun Cloning and Sequencing

Figure 11:
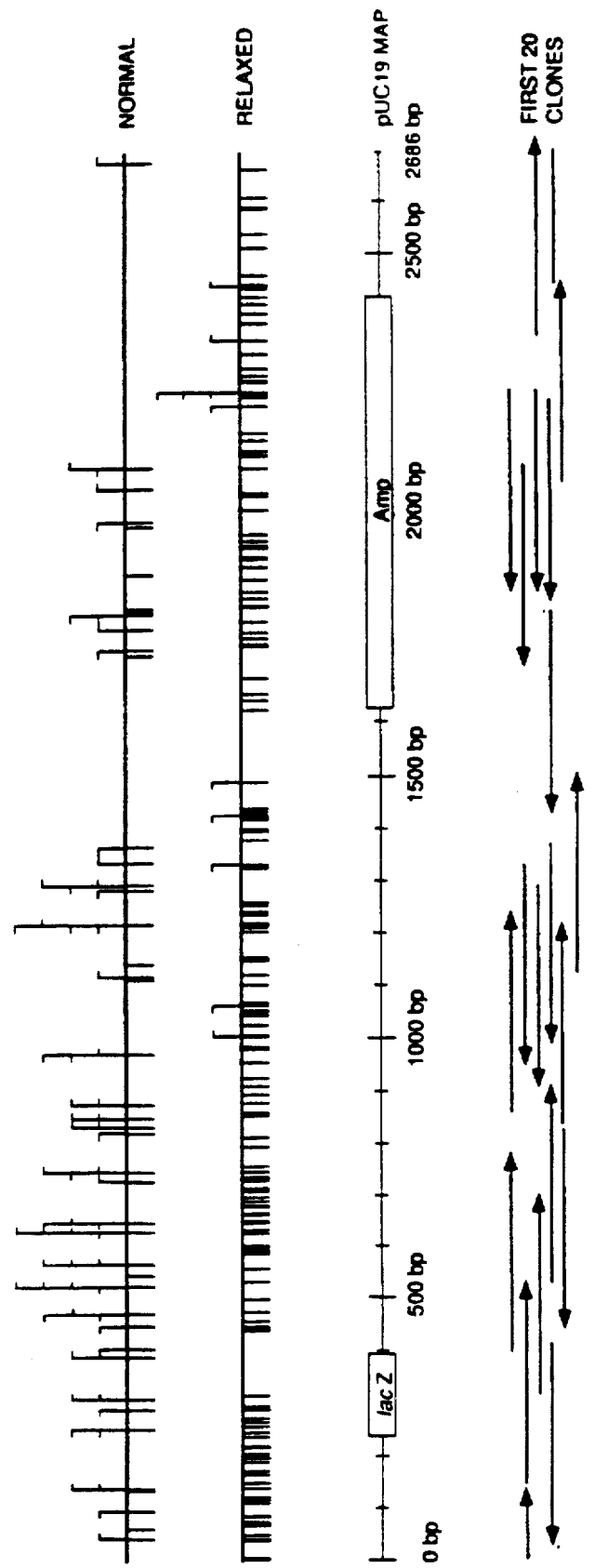
FIG. 11 is a schematic depiction of the distribution of CviJI sites in pUC19.

The ability of CviJI partial digestion to create uniformly representative clone libraries for DNA sequencing was tested on pUC19 DNA. pUC19 DNA was digested under CviJI conditions and size fractionated as described above. The fractionated DNA was cloned into the EcoRV site of M13SPSI, a lacZ minus vector constructed by adding an EcoRV restriction site to wild type M13 at position 5605. M13SPSI lacks a genetic cloning selection trait, therefore after ligation of the pUC19 fragments into the vector the sample was restricted with EcoRV to reduce the background of nonrecombinant plaques. Bacteriophage M13 plaques were picked at random and grown for 5–7 hours in 2 ml of 2XTY broth containing 20 µl of a DH5αF' overnight culture. After centrifugation to remove the cells, single-stranded phage DNA was purified using Sephaglass™ as specified by the manufacturer (Pharmacia LKB, Piscataway N.J.). The single-stranded DNA was sequenced by the dideoxy chain termination method using a radiolabeled M13-specific primer and Bst DNA polymerase (Mead et al., $Biotechniques$ 11:76–87 (1991)). The first 100 bases of 76 randomly chosen clones were sequenced to determine which CviJI recognition site was utilized, the orientation of each insert and how effectively the cloned fragments covered the entire molecule, as shown in FIG. 11. The positions of the 45 normal CviJI sites (PuGCPy) in pUC19 are indicated beneath the line labeled "NORMAL" in the FIG. 11. Similarly, the 160 CviJI* sites (GC) are indicated beneath the line labeled "RELAXED" in FIG. 11. The marks above these lines indicate the CviJI** pUC19 sites which were found in the set of 76 sequenced random clones. The frequency of cloning a particular site is indicated by the height of the line, and the left or right orientation of each clone is also indicated at the top of each mark. There are a total of 205 CviJI and CviJI* sites in pUC19.

The dam presented in FIG. 11 demonstrate that, under CviJI partial conditions, normal CviJI sites are preferentially restricted over relaxed (CviJI) sites. Of the 76 clones that were analyzed, only 13%, or 1 in 7, had sequence junctions corresponding to a relaxed CviJI* site. Thirty-five of the forty-five possible normal restriction sites were cloned, as compared to eight of the possible one hundred sixty relaxed sites. If the enzyme had exhibited no preference for normal or relaxed sites under the CviJI** partial conditions utilized here, then 78% of the sequence junctions analyzed should have been generated by cleavage at a relaxed CviJI* site. It may be noted that the relaxed CviJI* restriction sites that were found appear to be clustered in two regions of the plasmid that are deficient in normal CviJI sites. In addition, the combined distribution of the normal and relaxed sites which were restricted to generate the 76 clones appears to be quasi-random. That is, the longest gap between cloned restriction sites was no greater than 250 bp and no one particular site is over-utilized.

A detailed analysis of the distribution of CviJI** sequence junctions found from cloning pUC19 is presented in Table 5.

87%), or "normal" restriction sites, a significant fraction of the cleavage occurred at PyGCPy (about 6.5%) and PuGCPu (about 6.6%) sites, considering the short incubation times and limiting enzyme concentrations. The latter two categories of sites, and presumably the PyGCPu sites as well, are completely restricted under "relaxed" conditions, provided an excess of enzyme is present and sufficient time is allowed (see FIG. 7, and Xia et al., Nucleic Acids Res. 15:6075–6090 (1987)).

Digestion using CviJI treatment results in a relatively even distribution of breakage points across the length of the molecule (as shown in FIG. 11). As described above, FIG. 11 depicts a linear map of pUC19 showing the relative position of the lacZ' gene ($\alpha$ peptide of $\beta$-galactosidase gene) and ampicillin resistance gene (Amp). The marks extending beneath the top line (labeled "NORMAL") show the relative position of the 45 normal CviJI sites (PuGCPy) present in pUC19. The marks above the line are the cleavage sites found from sequencing the CviJI partial library. The height of the line indicates the number of clones obtained from cleavage at that site, and the orientation of the flag designates the right or left orientation of the respective clone. The marks extending beneath the second line (labeled "RELAXED") show the relative positions of the 160 CviJI* sites (GC) present in pUC19. Those marks above the line were found from sequencing the CviJI partial library. The bottom portion of FIG. 11 shows the relative position and orientation of the first 20 clones sequenced, assuming a 350 bp read per clone. CviJI cleavage at relaxed sites appears

TABLE 5

Distribution of Cloned CviJI** Partially-Digested pUC19 Sites.
NGCN

| Classification Group | Recognition Sequence | Site Distribution in PUC19 (%) | Cloned CviJI** Distribution (%) | Pu/Py Structure |
|---|---|---|---|---|
| Normal (N) | A C | AGCC 9 (4.4) | 13 (17.1) | |
| | G C | GGCC 11 (5.4) | 16 (21.1) | PuPuPyPy |
| | G T | GGCT 10 (4.9) | 12 (15.8) | |
| | | AGCT 15 (7.3) | 25 (32.9) | |
| | | 45 (22.0) | 66 (86.9) | |
| Relaxed (R$_1$) | C C | CGCC 11 (5.4) | 0 | |
| | G C | TGCC 12 (5.9) | 2 (2.6) | PyPuPyPy |
| | T T | TGCT 10 (4.9) | 1 (1.3) | |
| | | CGCT 22 (10.7) | 2 (2.6) | |
| | | 55 (26.9) | 5 (6.5) | |
| Relaxed (R$_2$) | A A | AGCA 16 (7.3) | 1 (1.3) | |
| | G C | GGCA 8 (3.9) | 0 | PuPuPyPu |
| | G G | AGCG 11 (5.4) | 0 | |
| | | GGCG 22 (10.7) | 4 (5.2) | |
| | | 57 (27.8) | 5 (6.6) | |
| Relaxed (R$_3$) | C A | CGCA 10 (4.9) | 0 | |
| | G C | TGCA 13 (6.3) | 0 | PyPuPyPu |
| | T G | CGCG 10 (4.9) | 0 | |
| | | TGCG 15 (7.3) | 0 | |
| | | 48 (23.4) | 0 | |

The GC sites in pUC19 may be divided into four classes based on their flanking Pu/Py structure. The fraction of GC sites observed in pUC19 which belong to each classification is roughly equal (22.0–27.8%). A striking difference was found between the observed distribution in pUC19 of normal and relaxed (R1, R2, R3) CviJI recognition sites and the distribution revealed by shotgun cloning and sequence analysis of CviJI**-treated DNA. While most of the sites cleaved by this treatment were found to be PuGCPy (about to be important in "filling gaps" left by normal restriction.

The primary goal of this effort was to determine the efficacy of these methods for rapid shotgun cloning and sequencing. For these purposes, only 100 bases of sequence dam were acquired per clone. However, if 350 bases of sequence had been determined from each clone, then the entire sequence of pUC19 would have been assembled from the overlap of the first 20 clones (FIG. 11). In this sequencing simulation 75% of pUC19 would have been sequenced at least 2 times from the first 20 clones. The highest degree of overfold sequencing would have been 6, and only involved 2.2% of the DNA. FIG. 11 also shows that most of the 1× sequencing coverage occurred in a region of the plasmid with a very low density of normal and relaxed CviJI restriction sites. Most of the single coverage occurs in a 240 bp region of the plasmid between 1490 bp and 1730 bp where there are only 4 CviJI relaxed sites. It should also be noted that by the 27th randomly picked clone most of this region would have been covered a second time.

Figure 12:
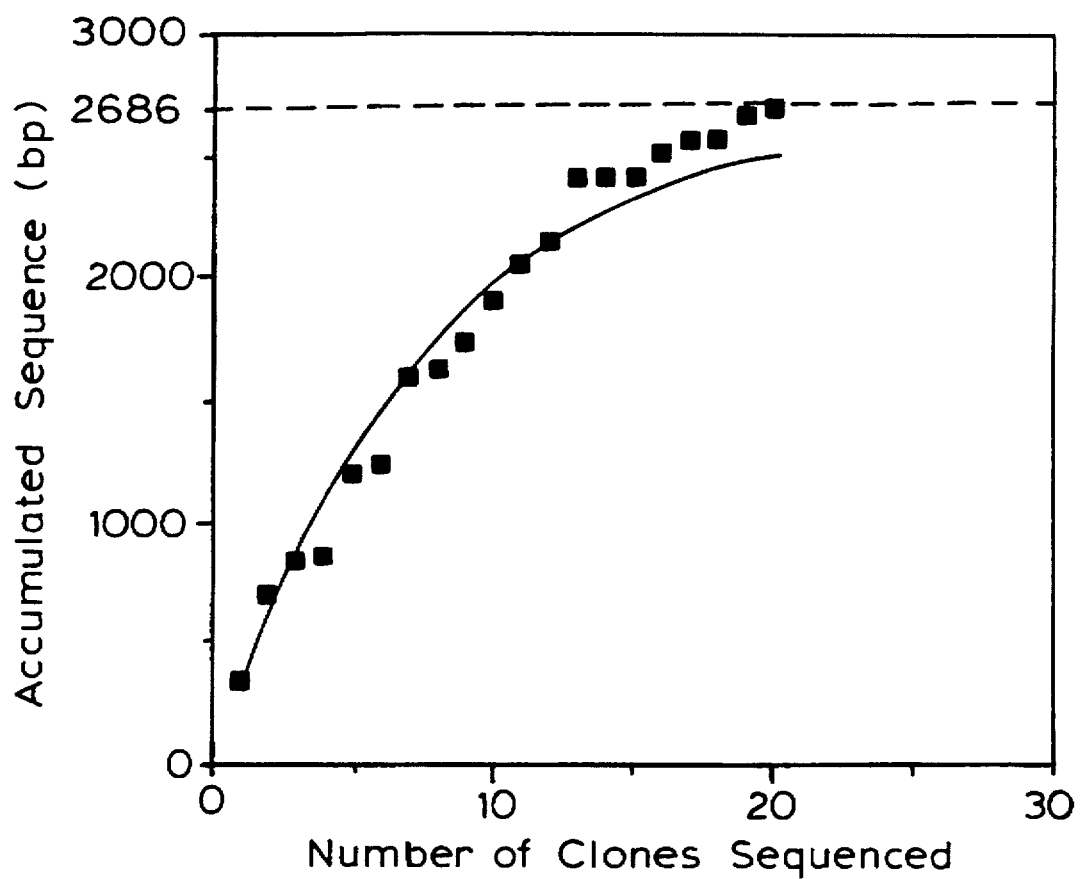
FIG. 12 is a graph of the rate of sequence accumulation by CviJI** shotgun cloning and sequencing.

Shotgun sequencing strategies are efficient for accumulating the first 80–95% of the sequence data. However, the random nature of the method means that the rate at which new sequence is accumulated decreases as more clones are analyzed. In FIG. 12 the total amount of unique pUC19 sequence accumulated was plotted as a function of the number of clones sequenced. The points represent a plot of the total amount of determined pUC19 sequence versus the total number of clones sequenced. The horizontal dashed line demarcates the 2686 bp length of pUC19. The smooth curve represents a continuous plot of the discrete function $S(N)=NLe^{-c\sigma}[((e^{c\sigma}-1)/c)+(1-s)]$. The theoretical accumulation curve expected for a process in which sequence information is acquired in a totally random fashion is also shown. The smooth curve is a continuous plot of the discrete function $S(N)$ where $$S(N)=NLe^{-c\sigma}[((e^{c\sigma}-1)/c+(1-\sigma)].$$

This equation is based upon the results developed by Lander et al., *Genomics* 2:231–239 (1988) for the progress of contig generation in genetic mapping. In the equation: N is the number of clones sequenced, L is the length of clone insert in bp, c is the redundancy of coverage or LN/G (where G is length of fragment being sequenced in bp), and $\sigma=1-\theta$, where $\theta$ is the fraction of length that two clones must share. The curve in FIG. 12 was calculated with G=2686 bp, L=350 bp, and $\sigma=1$. The plotted points lie close to the theoretical curve, and it thus appears that the sequence of pUC19 was accumulated in an apparent random fashion utilizing CviJI** fragmentation and column fractionation.

Example 18

Shotgun Cloning Utilizing 200 ng of Lambda DNA

Generally, 2–5 μg of DNA are needed for the sonication and agarose gel fractionation method of shotgun cloning in order to provide the several hundred colonies or plaques required for sequence analysis (Bankier et al. *Methods in Enzymol.* 155:51–93 (1987)). A ten-fold reduction in the amount of substrate required greatly simplifies the construction of such libraries, especially from large genomes, (Davidson, J. DNA *Sequencing and Mapping* 1:389–394 (1991)). The efficiency of constructing a large shotgun library from nanogram amounts of substrate was tested utilizing 200 ng of CviJI**-digested lambda DNA. This material was column-fractionated as described previously. In this case, ½ of the column eluant (15 μl containing 50 ng of DNA) was ligated to 100 ng of HincII-digested and dephosphorylated pUC19 as described in Example 15. The cloning efficiencies of the control DNAs were similar to those reported in Tables 2 and 3. The 50 ng cloning experiment yielded 230 white colonies per ligation reaction in one trial, and 410 white colonies per ligation reaction in a second trial. Thus, it should be possible to routinely construct useful quasi-random shotgun libraries from as little as 0.2–0.5 μg of starting material.

Example 19

Epitope Mapping

CviJI* recognizes the sequence GC (except for PyGCPu) in the target DNA. Under partial restriction conditions the length of fragment may be controlled by incubation time. Epitope mapping using CviJI** partial digests involves generating DNA fragments of 100–300 bp from a cDNA coding for the protein of interest, by methods described in Example 13, inserting them into an M13 expression vector, plating out on solid media, lifting plaques onto a membrane, screening for binding to the ligand of interest, and picking the positive plaques for isolation of the DNA, which is then sequenced to identify the epitope. Thus, the same epitope may be expressed as a small fragment or a larger fragment. This approach allows one to determine the smallest fragment containing the epitope of interest using functional assays such as binding to an antibody or other ligand, or using a direct assay for activity. For insertion into an M13 vector, linkers may be added to the fragments or the insert may be dephosphorylated to ensure that each fragment is cloned alone without ligation of multiple inserts.

The expression vectors recommended for subcloning of the CviJI fragments are Lambda Zap™ (Stratagene, LaJolla, Calif.) or bacteriophage M13-epitope display vectors. An advantage of using an M13-based vector is that the peptide or protein of interest may be displayed along with the M13 coat protein and does not require host cell lysis in order to analyze the protein of interest. The lambda-based vectors yield plaques and hence the protein can be directly bound to a membrane filter.

We claim:

1. A purified and isolated polynucleotide encoding a CviJI restriction endonuclease polypeptide or a variant thereof possessing restriction endonuclease activity characteristic of CviJI, said polynucleotide comprising a polynucleotide as set out in SEQ ID NO: 2.

2. The polynucleotide of claim 1 which is a DNA.

3. The DNA of claim 2 which is a viral genomic DNA sequence or a biological replica thereof.

4. The DNA of claim 2 which is a wholly or partially chemically synthesized DNA or biological replica thereof.

5. A purified isolated DNA encoding a polypeptide according to claim 1 by means of degenerate codons.

6. A vector comprising a DNA according to claim 2.

7. The vector of claim 6 which is the plasmid pCJH1.4 (ATCC Accession No. 69341).

8. A host cell stably transformed or transfected with a DNA according to claim 2 in a manner allowing the expression in said host cell of a CviJI polypeptide or a variant thereof possessing a recognition sequence specificity characteristic of CviJI.

9. The host cell according to claim 8, wherein said host cell is *E. coli*.

10. A method for producing a CviJI restriction endonuclease polypeptide or a variant thereof possessing biological activity specific to CviJI, said method comprising the steps of:

a) growing a transformed host cell containing a vector according to claim 6 in a suitable nutrient medium; and b) isolating the CviJI polypeptide or variant thereof from said host cell.

11. The method of claim 10 wherein said host cell is *E. Coli*.

* * * * *